United States Patent
Cook et al.

[19]

[11] Patent Number: 5,916,585
[45] Date of Patent: Jun. 29, 1999

[54] MATERIALS AND METHOD FOR THE IMMOBILIZATION OF BIOACTIVE SPECIES ONTO BIODEGRADABLE POLYMERS

[75] Inventors: Alonzo D. Cook; Paul D. Drumheller, both of Flagstaff, Ariz.

[73] Assignee: Gore Enterprise Holdings, Inc., Newark, Del.

[21] Appl. No.: 08/865,800

[22] Filed: May 30, 1997

Related U.S. Application Data

[63] Continuation-in-part of application No. 08/657,083, Jun. 3, 1996, abandoned.

[51] Int. Cl.[6] .................................................... A61F 2/28
[52] U.S. Cl. .............................. 424/426; 523/115; 623/16
[58] Field of Search .............................. 424/426; 623/16; 523/115

[56] References Cited

U.S. PATENT DOCUMENTS

| | | |
|---|---|---|
| 4,113,912 | 9/1978 | Okita . |
| 4,181,983 | 1/1980 | Kulkarni . |
| 4,193,138 | 3/1980 | Okita . |
| 4,389,330 | 6/1983 | Tice et al. . |
| 4,442,133 | 4/1984 | Greco et al. . |
| 4,619,897 | 10/1986 | Hato et al. . |
| 4,745,160 | 5/1988 | Churchill et al. . |
| 4,749,585 | 6/1988 | Greco et al. . |
| 4,879,135 | 11/1989 | Greco et al. . |
| 4,946,686 | 8/1990 | McClelland et al. . |
| 5,001,009 | 3/1991 | Whitbourne . |
| 5,041,138 | 8/1991 | Vacanti et al. . |

(List continued on next page.)

FOREIGN PATENT DOCUMENTS

| | | |
|---|---|---|
| 0426486A2 | 5/1991 | European Pat. Off. . |
| 0604022 | 6/1994 | European Pat. Off. . |
| 0705878 | 4/1996 | European Pat. Off. . |
| 2000978 | 1/1979 | United Kingdom . |
| 88/02623 | 4/1988 | WIPO . |
| 89/11500 | 11/1989 | WIPO . |
| 90/05755 | 5/1990 | WIPO . |
| 90/12603 | 11/1990 | WIPO . |
| 90/12604 | 11/1990 | WIPO . |
| 92/00747 | 1/1992 | WIPO . |

(List continued on next page.)

OTHER PUBLICATIONS

Bachtsi, A.R., Kiparissides, C. Synthesis and release studies of oil–containing poly(vinyl Alchohol) Microcapsules prepared by coacervation. Journal of Controlled Release 1996; 38:49–58.

Brinkley, M. A Brief Survey of Methods for Preparing Protein Conjugates with Dyes, Haptens, and Cross–Linking Reagents. Bioconjugate Chem. 1992;3:2–13.

Danielson, N.D., Siergiej, R.W. Immoblization of Enzymes on Polytetrafluoroethylene Particles Packed in HPLC Columns. Biotechnology and Bioengineering 1981;23:1913–1917.

(List continued on next page.)

*Primary Examiner*—Carlos Azpuru
*Attorney, Agent, or Firm*—Eric J Sheets

[57] ABSTRACT

The present invention is directed to hydrophobic biodegradable polymeric materials having at least one surface thereof rendered more hydrophilic by attachment of at least one layer of a hydrophilic polymer thereto. The hydrophilic polymer layer is cross-linked together on the surface of the biodegradable material with a cross-linking agent or scheme that is biodegradable. Bioactive species are immobilized to chemically functional groups of the components of the first layer or to unreacted chemically functional groups of the cross-linking agent. Optionally, the bioactive species may be reversibly immobilized through chemically functional linkages that are degradable. The result is an implantable construction with immobilized bioactive species having structural components that are all subject to degradation in the body of a recipient.

75 Claims, 3 Drawing Sheets

U.S. PATENT DOCUMENTS

| | | |
|---|---|---|
| 5,041,225 | 8/1991 | Norman . |
| 5,049,403 | 9/1991 | Larm et al. . |
| 5,069,899 | 12/1991 | Whitbourne et al. . |
| 5,084,051 | 1/1992 | Törmälä et al. . |
| 5,128,170 | 7/1992 | Matsuda et al. . |
| 5,209,850 | 5/1993 | Abayasekara et al. . |
| 5,213,898 | 5/1993 | Larm et al. . |
| 5,217,492 | 6/1993 | Guire et al. . |
| 5,240,747 | 8/1993 | Matsuda et al. . |
| 5,263,992 | 11/1993 | Guire . |
| 5,278,063 | 1/1994 | Hubbell et al. . |
| 5,308,641 | 5/1994 | Cahalan et al. . |
| 5,330,911 | 7/1994 | Hubbell et al. . |
| 5,344,455 | 9/1994 | Keogh et al. . |
| 5,352,511 | 10/1994 | Abayasekara et al. . |
| 5,354,587 | 10/1994 | Abayasekara . |
| 5,369,012 | 11/1994 | Koontz et al. . |
| 5,391,423 | 2/1995 | Wnuk et al. . |
| 5,399,665 | 3/1995 | Barrera et al. . |
| 5,415,938 | 5/1995 | Calahan et al. . |
| 5,429,839 | 7/1995 | Gravier et al. . |
| 5,443,950 | 8/1995 | Naughton et al. . |
| 5,447,724 | 9/1995 | Helmus et al. . |
| 5,470,829 | 11/1995 | Prisell et al. . |
| 5,512,474 | 4/1996 | Clapper et al. . |
| 5,525,348 | 6/1996 | Whitbourne et al. . |

FOREIGN PATENT DOCUMENTS

| | | |
|---|---|---|
| 92/07899 | 5/1992 | WIPO . |
| 92/13718 | 8/1992 | WIPO . |
| 93/07913 | 4/1993 | WIPO . |
| 93/16176 | 8/1993 | WIPO . |
| 93/20859 | 10/1993 | WIPO . |
| 94/01468 | 1/1994 | WIPO . |
| 94/09760 | 5/1994 | WIPO . |
| 94/25079 | 11/1994 | WIPO . |
| 95/28124 | 10/1995 | WIPO . |
| 96/10426 | 4/1996 | WIPO . |
| 96/10428 | 4/1996 | WIPO . |
| 96/30060 | 10/1996 | WIPO . |

OTHER PUBLICATIONS

Fan, Y.L. Hydrophilic Polymers (For Friction Reduction). *Polymeric Materials Encyclopedia.* Boca Raton: CRC Press. 1996; Vol. 5 (H–L), pp. 3107–3115.

Ficek, B.J., Peppas, N.A. Novel Preparation of Poly(vinyl alcohol) Microparticles Without Crosslinking Agent For Controlled Drug Delivery. Mat. Res. Soc. Symp. Proc. 1994;331:223–226.

Hermanson, G. T., Mallia, A.K., Smith, P.K. *Immobilized Affinity Ligand Techniques.* San Diego: Academic Press, Inc. 1992;Chapter 2 and 3, pp. 51–279.

Hertzberg, S., et al. Mixed photo–cross–linked polyvinyl alcohol and calcium–alignate gels for cell entrapment. Appl. Microbiol. & Biotechnol. 1995;v43 n1:10–17.

Hirano, Y., et al. Cell–attachment activities of surface immobilized oligopeptides RGD, RGDS, RGDV, RGDT, and YIGSR toward five cell lines. J. Biomater. Sci. Polymer Edn. 1993;v4 n3:235–243.

Horton, H., Swaisgood, H.E. Covalent Immobilization of Proteins by Techniques Which Permit Subsequent Release. *Methods In Enzymology: Immobilized Enzymes and Cells. Part B.* Orlando: Academic Press, Inc. 1987;135: Chapter 9, pp. 130–141.

Ito, Y., Inoue, S.Q., Imanishi, Y. Cell growth on immobilized cell growth factor. 6. Enhancement of fibroblast cell growth by immobilized insulin and/or fibronectin. Journal of Biomedical Materials Research 1993;27:901–907.

Ito, Y., Kajihara, M., Imanishi, Y. Materials for enhancing cell adhesion by immobilization of cell–adhesive peptide. Journal of Biomedical Materials Research 1991;25:1325–1337.

Ito, Y., et al. Synthesis and nonthrombogenicity of poly-etherurethaneurea film grafted with poly(sodium vinyl sulfonate). Journal of Biomedical Materials Research 1991;25:1347–1361.

Kanazawa, S. et al. Development of a Hydrophilic PTFE Porous Membrane Filter. Sumimoto Denki Sept. 1995;n 147:90–95.

Karel, S.F., Libicki, S.B., Robertson, C.R. The Immobilization of Whole Cells: Engineering Principles. Chemical Engineering Science 1985; v40 n8:1321–1354.

Kobayashi, H., Ikada, Y. Covalent immobilization of proteins on to the surface of poly(vinyl alcohol) hydrogel. Biomaterials Oct. 1991; 12:747–751.

Kondoh, A., Makino, K., Matsuda, T. Two–Dimensional Artificial Extracellular Matrix: Bioadhesive Peptide–Immobilized Surface Design. Journal of Applied Polymer Science 1993;47:1983–1988.

Kung, I.M. et al. Surface modifications of alginate/poly(L–l-ysine) microcapsular membranes with poly(ethylene glycol) and poly(vinyl alcohol). Biomaterials 1995; v16 n8:649–655.

Lin, H–B., Cooper, S.L. Polyurethane copolymers containing covalently attached RGD–Peptide: synthesis and cell adhesion studies. Mat. Res. Soc. Symp. Proc. 1992;252:185–192.

Massia, S.P., Hubbell, J.A. Human endothelial cell interactions with surface–coupled adhesion peptides on a nonadhesive glass substrate and two polymetric biomaterials. Journal of Biomedical Materials Research 1991;25:223–242.

Massia, S.P., Hubbell, J.A. Tissue engineering in the vascular graft. Cytotechnology 1992; 10:189–204.

Mooney, D.J., et al. Biodegradable sponges for hepatocyte transplantation. Journal of Biomedical Materials Research 1995; 29:959–965.

Nakajima, K. et al. Adsorption of Plasma Proteins on Arg–Gly–Asp–Ser Peptide–Immobilized Poly(vinyl alcohol) and Ethylene–Acrylic Acid Copolymer Films. Polymer Journal 1990;v22 n11:985–990.

Ozaki, K.C., et al. Glycoconjugate mediated endothelial cell adhesion to Dacron polyester film. Journal of Vascular Surgery 1993; v18 n3:486–494.

Park, K., Shalaby, W.S.W, Park, H., Eds., *Biodegradable Hydrogels for Drug Delivery.* Lancaster: Technomic Publishing Co., Inc. 1993;233–241.

Wintermantel, E., et al. Tissue engineering scaffolds using superstructures. Biomaterials 1996; 17:83–91.

Wong, S.S. *Chemistry of Protein Conjugations and Cross–Linking.* Boca Raton: CRC Press, Inc. 1993;1–325.

Wu, S. *Surface and Interfacial Tensions of Polymers, Oligomers, Plasticizers, and Organic Pigments.* 441–426.

Cook, Alonzo D. The Evaluation of RGD–Peptide Modified Poly(lactic acid–co–lysine) as a Resorbable, Interactive Biomaterial. Massachusetts Institute Of Technology, Feb. 1996.

MATERIALS AND METHOD FOR THE IMMOBILIZATION OF BIOACTIVE SPECIES ONTO BIODEGRADABLE POLYMERS

This application is a continuation-in-part of application Ser. No. 08/657,083, filed Jun. 3, 1996 now abandoned.

FIELD OF THE INVENTION

The present invention relates to the modification of bioabsorbable polymers to render the absorbable polymers more hydrophilic and to provide functional attachment sites for the immobilization of bioactive species onto the absorbable polymeric substrates.

BACKGROUND OF THE INVENTION

Implantable polymeric materials capable of being degraded and absorbed by the body have been in use for many decades. These biodegradable materials are often used as structural supports, such as scaffolds for guiding tissue regeneration, as sutures, staples, and meshes, as protective barriers during wound healing, or as a means for delivering therapeutical substances to a recipient in a controlled fashion.

The degradation of these polymers in vivo may occur through a variety of mechanisms. For example, the covalent linkages in a biodegradable polymer may be labile to enzymatic cleavage or non-enzymatic hydrolysis. The product of the hydrolysis may or may not be soluble in water. Water-soluble products are often excreted directly from the body or are removed from the body after passing through a particular metabolic pathway. For water-insoluble products, the phagocytotic action of cells, such as macrophages and/or foreign body giant cells, may play a major part in degrading and eliminating the products. Such phagocytotic biodegradation usually involves the invocation of an inflammatory response to the biodegradable material by the recipient.

When biodegradable materials are implanted in a recipient and used as structural supports, there is often an ingrowth of cells from the recipient into the space occupied by the material as the material degrades and is removed from the body of the recipient. In some circumstances, fairly complex, three-dimensional, tissue structures can be grown this way. One example is the regeneration of cartilage, which is accomplished by pre-seeding a degradable fiber mesh with chondrocytes, and after several weeks of culturing the cells in vitro, implanting the constructs in a recipient (see U.S. Pat. No. 5,041,138, issued to Vacanti, et. al., for example). Another example is the regeneration of dermis using fibroblasts seeded on a degradable polymer scaffold (see U.S. Pat. No. 5,443,950, issued to Naughton, et. al., for example).

To effect controlled release of a therapeutical agent from a biodegradable polymer, the therapeutical agent is usually admixed with the particular biodegradable polymer during manufacture of the controlled release material. Following implantation of the material in a recipient, the therapeutical agent is released from the biodegradable polymer as the polymer is degraded by the body of the recipient (see U.S. Pat. No. 4,389,330, issued to Tice et al., for example). The rate of degradation of a biodegradable polymer is dependent on the chemical composition of the polymer, the crystallinity of the sample, the porosity, and the wettability. For example, hydrophobic biodegradable polymers usually degrade at a slower rate than hydrophilic biodegradable polymers.

Since most biodegradable materials, such as poly(alpha-hydroxy esters), are relatively hydrophobic, it may be desirable to modify the materials to render the surfaces thereof more hydrophilic. By making the surfaces more hydrophilic, the degradation rate of the polymer may be increased, cell attachment may be enhanced, or protein deposition patterns may be altered in such a manner as to improve the biocompatibility or cell response to the polymer.

Hydrophobic surfaces are low energy surfaces that are readily wetted by low surface tension fluids, such as low molecular weight hydrocarbons or alcohols, and most low molecular weight organic solvents, such as benzene, acetone, toluene, and dioxane, etc. Hydrophilic surfaces, on the other hand, are high energy surfaces that are readily wetted by high surface tension fluids. Examples of high surface tension fluids include, but are not limited to, liquid water, aqueous salt and protein solutions, dimethyl formamide, dimethyl sulfoxide, glycerol, hexamethyl phosphorictriamide, formamide, and ethylene glycol, for example.

Table 1 lists examples of polymeric materials in order of increasing surface tension, with representative values of the surface tension (dyn/cm) for each material measured at 20° C. (Polymer Handbook, 3rd Edition, J. Brandrup, E. H. Immergut, Eds., John Wiley & Sons, Inc., pp. VI411–VI426, 1989). In general, the surface tension of polymeric materials ranges from about 10 to 70 dyn/cm. Many polymers have intermediate surface energies and the wetting behavior of high surface tension fluids on these polymers is dependent on factors such as functional groups, surface roughness, contamination, and surface mobility in addition to the surface tension of the polymer surface.

TABLE 1

| Polymer | Surface Tension (dyn/cm) |
|---|---|
| poly(hexafluoropropylene) | 17 |
| poly(dimethyl siloxane) | 20 |
| poly(tetrafluoroethylene) | 24 |
| poly(trifluoroethylene) | 27 |
| poly(vinylidine fluoride) | 33 |
| poly(vinyl alcohol) | 37 |
| poly(styrene) | 40 |
| poly(methyl methacrylate) | 41 |
| poly(vinyl chloride) | 42 |
| poly(ethylene terephthalate) | |
| poly(hydroxyethyl methacrylate) (40% water) | 69 |

Source: Polymer Handbook, 3rd Edition, J. Brandrup, E.H. Immergut, Eds., John Wiley & Sons, Inc., pp. VI411–V426, 1989. Values were determined at 20° C.

One method to compare the hydrophobicity of a non-porous, solid surface of one material with the non-porous, solid surface of another material is to orient the material horizontally and apply a droplet of distilled water to the surface of the material. The angle which the edge of the water droplet makes with the surface is the advancing contact angle or simply the "contact angle." For most hydrophobic materials, the contact angle will be above 90°. For example, the contact angle of water on poly (tetrafluoroethylene) is approximately 120°. For most hydrophilic materials, the contact angle will be below about 30°. For example, the contact angle of water on poly (hydroxyethyl methacrylate) is approximately 15°. For the purposes of this invention, solid materials which have been modified with one or more layers of hydrophilic polymers will be considered having been rendered hydrophilic if the contact angle decreases by 10° or more. A preferred result would be a resulting contact angle less than 30°.

For porous materials, a simple test to compare the wettability of one material with another is to position the material horizontally and apply a droplet of distilled water onto the surface of the material. For most hydrophobic, porous materials, the water droplet will remain on the surface. For most hydrophilic, porous materials, the water droplet will immediately penetrate into the pores of the sample. The fibers or polymer strands which form the sides of the pores act as hydrophilic surfaces which the water spreads on. The pores attract the water droplet by capillary action. For the purposes of this invention, porous materials which wet within 1 second after exposure to a droplet of water are considered hydrophilic. Porous materials which do not spontaneously wet, which require more than 1 second to wet, or which require mechanical agitation to thoroughly wet, are considered hydrophobic.

It is known to treat non-biodegradable materials, such as polytetrafluoroethylene, with surfactants or other hydrophilic polymers to render the surfaces of these materials more hydrophilic and often wettable with liquid water. Such a surfactant treatment is often unstable, however, with the surfactant easily leaching from the hydrophobic material when in use. A more stable surfactant coating can be made on hydrophobic materials by cross-linking the components of the surfactant together on the material (see U.S. Pat. No. 4,113,912, issued to Okita, for example).

A stable coating of a hydrophilic material on a hydrophobic biodegradable material would be undesirable, however, because the cross-linked hydrophilic material would most likely remain intact in a recipient after the biodegradable material to which it was initially applied had degraded and been removed from the body of the recipient. For example, a method to render biodegradable polymers more wettable has been described by Mooney, et. al. (Mooney, D. J., Park, S., Kaufmann, P. M., Sano, K., McNamara, K., Vacanti, J. P., Langer, R., "Biodegradable sponges for hepatocyte transplantation", J. *Biomed. Mat. Res.,* 29:959–965, (1995)). Porous sponges fabricated from poly(L-lactic acid) (PLA) were rendered more hydrophilic by adding the surfactant poly(vinyl alcohol) (PVA) to the interior surfaces of the porous PLA sponges. The addition of PVA increased the wettability of the polymer sponge and resulted in a more thorough infiltration and a more extensive seeding of the sponge with hepatocytes than occurred with untreated sponges. Mooney, et. al. also described the use of commercially available PVA sponges as cell transplantation devices, but this approach was discounted by Mooney, et. al. as unsuitable due to the non-degradable nature of covalently cross-linked PVA. Methods to reversibly cross-link or otherwise transiently stabilize the PVA coating on the PLA sponge were not described.

The hydrophobicity of biodegradable polymers also presents a problem when it is desired to immobilize a bioactive species onto the surface of a device made from a biodegradable material, rather than incorporate the bioactive species into the biodegradable material. In the simplest method, for example, a bioactive species is immobilized onto the surface of a biodegradable polymer via simple physicochemical adsorption (physisorption). However, physisorption of bioactive species is often kinetically and thermodynamically unstable, highly reversible, and competitively displaced by solution phase reactants, products, or nutrients. Thus, physisorption of bioactive species to biodegradable materials is not usually a suitable immobilization technique.

The term "immobilize," and its derivatives, as used herein refers to the attachment of a bioactive species directly to a biodegradable support member or to a biodegradable support member through at least one intermediate component. As used herein, the term "attach" and its derivatives refer to adsorption, such as, physisorption, or chemisorption, ligand/receptor interaction, covalent bonding, hydrogen bonding, or ionic bonding of a polymeric substance or a bioactive species to a biodegradable support member.

"Bioactive species" include enzymes, organic catalysts, ribozymes, organometallics, proteins, glycoproteins, peptides, polyamino acids, antibodies, nucleic acids, steroidal molecules, antibiotics, antimycotics, cytokines, carbohydrates, oleophobics, lipids, extracellular matrix and/or its individual components, pharmaceuticals, and therapeutics, for example. Cells, such as, mammalian cells, reptilian cells, amphibian cells, avian cells, insect cells, planktonic cells, cells from non-mammalian marine vertebrates and invertebrates, plant cells, microbial cells, protists, genetically engineered cells, and organelles, such as mitochondria, are also bioactive species. In addition, non-cellular biological entities, such as viruses, virenos, and prions are considered bioactive species.

Bioactive species could be attached to a hydrophobic biodegradable polymer through chemically functional groups on the components of the polymer. However, many biodegradable polymers lack free chemically functional groups altogether or have such reduced numbers that significant quantities of bioactive species cannot be immobilized thereto. For example, the biodegradable polymers poly(lactic acid) and poly(glycolic acid) do not contain any chemically functional groups along the hydrocarbon backbone of the materials to which a bioactive species can be covalently coupled. One strategy that has been proposed for introducing functional groups into poly(lactic acid) is the copolymerization of lactide with a cyclic monomer of lactic acid and the amino acid lysine to create poly(lactic acid-co-lysine) (see U.S. Pat. No. 5,399,665, issued to Barrera, et. al.). This copolymer provides side chains that terminate in amino ($NH_2$) groups. These amino groups can be used as attachment sites for the immobilization of bioactive species. Since this method chemically alters the polymer, many of the properties of the polymer are subject to change. For example, the degradation rate and the tensile strength may be effected by the alteration to the polymer. The processing of the polymer may also be effected by altering the hydrocarbon backbone of the polymer.

Prisell et al., in U.S. Pat. No. 5,740,829, have attempted to immobilize proteins onto the surface of a biodegradable material by first physisorbing the protein onto the biodegradable material, followed by cross-linking the proteins together on the surface. In the method, proteins, such as bone morphogenetic protein (BMP) or insulin-like growth factor-1-receptor (IGF-1 receptor), were adsorbed onto biodegradable polymers, such as poly(glycolic acid) (PGA) or poly(lactic acid) (PLA), and cross-linked in place using imidocarbonates, carbonates, oxiranes, aziridine, activated double bonds, or halogens. This method often results in a very inefficient immobilization, however. In addition, the cross-linked proteins often have a marked decrease in bioactivity. Accordingly, this approach is usually unsuitable for immobilization of bioactive species to a biodegradable support member.

Stable immobilization of bioactive species onto a hydrophobic support member, such as porous polytetrafluoroethylene, is taught by Drumheller in U.S. patent application Ser. No. 08/660,698, filed Jun. 3, 1996. In this method, hydrophobic surfaces, inter alia, are rendered hydrophilic and wettable with liquid water by attaching a surfactant material to the hydrophobic surface and cross-linking the surfactant together, forming a first layer thereon. Additional layers of hydrophilic polymers are attached to the first layer to amplify the number of chemically functional groups available for the subsequent immobilization of bioactive species thereto. It would be undesirable to stably immobilize a bioactive species on an implantable biodegradable material according to the method of Drumheller because the bioactive species and its immobilization scaffold will most often remain intact in a recipient after the biodegradable support it has been applied to has degraded and been removed from the body of the recipient.

A normally hydrophobic biodegradable material having surfaces that are rendered more hydrophilic with a hydrophilic material that is initially stable on the surface of the biodegradable material, but is itself subject to degradation upon implantation in a recipient would be useful. Such a material with bioactive species immobilized thereto would also be useful. Ideally, constructs used to render hydrophobic biodegradable materials hydrophilic and amenable to immobilization of bioactive species thereto would be transitory in nature and not remain intact in the body of a recipient substantially longer than the biodegradable material. There is a need, therefore, for a biodegradable material having hydrophobic surfaces that are rendered more hydrophilic with hydrophilic polymeric materials that are biodegradable and to which bioactive species can be readily immobilized.

SUMMARY OF THE INVENTION

The present invention is directed to hydrophobic biodegradable polymeric materials, or support members, having at least a portion of at least one surface thereof rendered more hydrophilic by attachment of at least one layer of a hydrophilic polymer thereto. The first hydrophilic polymer layer is cross-linked together on the surface of the biodegradable support member with a cross-linking agent that is biodegradable or with a cross-linking scheme that is transient and non-covalent in nature. Bioactive species are immobilized to chemically functional groups of the first hydrophilic polymer layer or to unreacted chemically functional groups of the cross-linking agent used in forming the first layer. On one embodiment, the bioactive species may be reversibly immobilized through chemically functional linkages that are degradable. Optionally, additional layers of hydrophilic polymers may be attached to the first hydrophilic polymer layer and bioactive species immobilized to at least one of the additional layers. The result is an implantable construction with immobilized bioactive species having structural components that are all subject to degradation in the body of a recipient.

Biodegradation of the structural components of the present invention is accomplished by enzymatic cleavage or non-enzymatic hydrolysis of the cross-linking compounds or by the reversal of the non-covalent cross-linker linkages to a non-crosslinked state. Optionally, the components of the hydrophilic polymer may be biodegradable as well. Preferably, the biodegradation products are able to be cleared by normal physiological processes, such as elimination in the kidneys or lungs or through catabolism in the liver.

In the present invention, a polymeric surfactant is attached onto a support member comprised of a biodegradable material. The surfactant is cross-linked together with a cross-linking agent that forms cleavable covalent bonds between the surfactant polymers, thereby forming a first layer on the support member. Alternatively, the surfactant is cross-linked on the support member to form a first layer thereon by using transient non-covalent cross-linking schemes. Following cross-linking, the first layer is initially physically and chemically stable. The first layer renders the hydrophobic surface of a biodegradable support member more hydrophilic. Bioactive species are immobilized via the chemically functional groups of the surfactant polymer of the first layer (see FIG. 1) or through unreacted chemically functional groups of the cross-linking agent (see FIG. 2). Under in vivo conditions, both the first layer and the biodegradable support member are subject to degradation and/or elimination.

Optionally, additional layers of hydrophilic material comprised of at least one type of hydrophilic polymer can be attached to the first layer and bioactive species immobilized to at least one of the layers. The hydrophilic polymers of the additional layers can be attached to the first layer through chemically functional groups of the surfactant polymer or through unreacted chemically functional groups of the cross-linking agent. Bioactive species are immobilized to at least one of the additional layers of hydrophilic polymers through chemically functional groups on the polymers (see FIG. 3). In addition to serving as a substrate for immobilization of a bioactive species, additional layers of hydrophilic polymers can serve to enhance the hydrophilic properties of the construction and/or as a permeable protective covering for the bioactive species.

Referring to FIG. 1, one embodiment of the present invention (10) is directed to a biodegradable material having immobilized bioactive species comprising a biodegradable support member (12); a first layer (14) comprised of at least one species of a polymeric surfactant attached to the support member and cross-linked together with a cross-linking agent that forms cleavable covalent bonds in the first layer; and at least one type of bioactive species (16) attached to the first layer. Alternatively, the polymeric surfactant may be cross-linked via a reversible, non-covalent, cross-linking scheme.

While the present invention has wide application, it is particularly suitable for transient immobilization of insulin secreting pancreatic islet cells or genetically engineered insulin secreting cells. Transient immobilization of such cells may be useful for facilitating transplantation or implantation of the cells into a recipient as a means for treating or ameliorating diabetes mellitus. The present invention is also suitable for the transient immobilization of renal epithelial or interstitial cells for use in renal failure therapy. Further uses include the controlled release of immobilized bioactive species including, but not limited to, anti-coagulant factors, such as heparin, heparan sulfate, tPA, protein S, urokinase, and protein C, etc. onto a synthetic vascular graft, vascular stent, or vascular stent-graft for improvement of vascular patency; and immobilization of pro-coagulant factors, such as tissue factor, von Willebrand factor, factor XIII, kininogen, and thrombin, etc. onto surgical sutures, surgical mesh materials, or anastomotic wraps, for example. The present invention is also suitable for the transient immobilization of adhesion-dependent or adhesion-independent cell lines comprising genetically engineered cells for use in genetic therapy; the transient immobilization of adhesion-dependent or adhesion-independent cell lines for use in transplantation therapy; the transient immobilization of pro-adhesive ligands, such as the tripeptide Arg-Gly-Asp, collagens, and fibronectin, for example, in order to promote adhesion, spreading, and/or migration of cellular bioactive species; the transient immobilization of bone morphogenetic protein, and other morphogens or growth factors, for example, in order to promote proliferation or differentiation of cellular bioactive species; the transient immobilization of anti-adhesive ligands, such as dextran, albumin, and polyethylene glycol, for example, in order to reduce non-specific cellular adhesion to biodegradable materials, such as surgical sutures, surgical meshes, and anastomotic wraps; the transient immobilization of antimicrobial agents to prevent device-associated infections; and the transient immobilization of bacteria or yeast cells for use in bioremediation and biotechnology. The present invention is particularly suitable for transient immobilization of stromal and/or parenchymal cells for guided tissue regeneration of organs and tissues such as liver, skin, gingiva, cartilage, bone, periodontal ligament, blood vessels, trachea, esophagus, nerves, ureters, and intestine, for example. In addition to transient immobilization of bioactive species, the present invention is suitable for use as a temporary scaffold for cell transplantation.

One advantage of the present invention over currently available materials is the ability to attach pharmaceutical agents to a biodegradable support member in order to provide local or systemic delivery of drugs, or to control bacterial infection or inflammation, for example. The attachment of pharmaceutical agents through cleavable immobilization chemistries enables the pharmaceutical agent to be released in a controlled manner, followed by degradation and removal of the remaining components of the present invention from the recipient without need for surgical intervention.

The present invention is useful in an implantable hybrid artificial organ design as a temporary scaffold for cells. The present invention is also useful in extracorporeal organ assist devices as a physical support for cells. in these systems, as the cells mature and respond to the needs of the body, the material of this invention first simply provides physical support. Over time, the polymeric support degrades and the cells synthesize extracellular matrix proteins. The cells replace the biodegradable support member with extracellular matrix proteins that then serve as their underlying physical support.

The present invention is also directed to methods for rendering the surfaces of a hydrophobic biodegradable material hydrophilic by elevating the surface energy of these materials to support wetting and spreading of high surface tension fluids thereon. The present invention is also directed to methods for reversibly immobilizing bioactive species to the hydrophilic surfaces formed on the biodegradable material.

Another advantage of the present invention is the preservation of the mechanical properties of the underlying support. In contrast to other approaches to provide functional groups for subsequent attachment of bioactive species (e.g. Barrera, U.S. Pat. No. 5,399,665), this invention does not alter the molecular chains of the support polymer, which alteration can lead to a decrease in mechanical integrity.

DETAILED DESCRIPTION OF THE INVENTION

Figure 1:
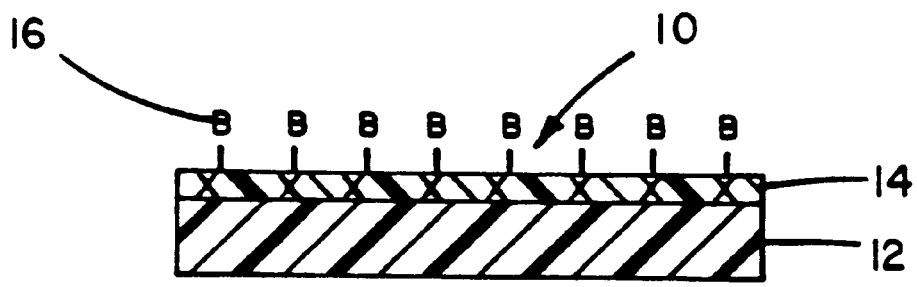
FIG. 1 illustrates a cross-section of the present invention (10) having a first layer (14) attached to a support member (12) wherein bioactive species (16) are immobilized directly to chemically functional groups of the first layer. The letter "x" indicates that the constituents of the first layer are cross-linked together.
Figure 2:
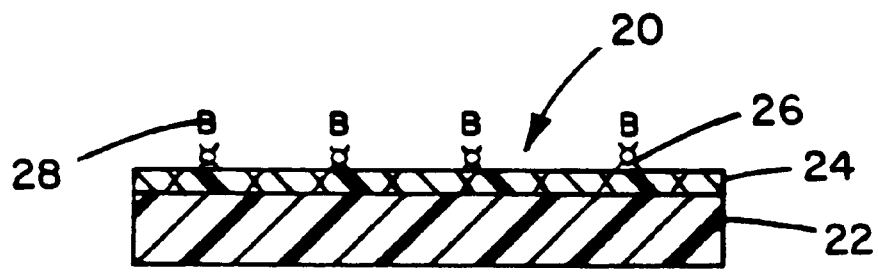
FIG. 2 illustrates a cross-section of the present invention (20) having a first layer (24) attached to a support member (22) wherein the letter "x" indicates that the constituents of the first layer are cross-linked together and the symbol ¤ (26) indicates unreacted chemically functional groups of the cross-linking agent to which bioactive species (28) are attached.

As described in the Background Section, prior methods for the immobilization of bioactive species to support members comprised of hydrophobic biodegradable polymer based materials are problematic. The present invention resolves the above-described problems with a construction that provides a hydrophilic polymeric coating, or first layer, for a biodegradable support member that is initially stable. The first layer is subject to biodegradation along with the support member under in vivo conditions. Stability is provided to the first layer by cross-linking the hydrophilic polymers together with a suitable cross-linking agent. A suitable covalent cross-linking agent in the present invention is one that forms covalent bonds between the hydrophilic polymers of the first layer that are cleavable under in vivo conditions or under conditions that simulate an in viva environment. Alternatively, non-covalent cross-linking of the hydrophilic polymers is accomplished by inducing transient non-covalent cross-links using such methods as complexation, coacervation, and hydrogen-bonding. Bioactive species are then immobilized to the first layer through chemically functional groups of the hydrophilic polymer coating or through unreacted chemically functional groups of the cross-linking agent.

For porous support members comprised of hydrophobic biodegradable polymer based materials, the present invention also permits bioactive species to be readily immobilized on the surfaces defining the porous regions of the support member without significantly reducing the porosity of the support member. The result is a biodegradable support member having surfaces rendered hydrophilic and wettable with high surface tension fluids throughout its bulk to which at least one type of bioactive species is immobilized.

In a preferred embodiment of the present invention, the construction is assembled from the following components: a support member comprised of a biodegradable polymeric material; a first layer comprised of at least one species of a polymeric surfactant, or a multifunctional copolymer, comprised of at least one domain that has a physicochemical affinity for the support member to allow physicochemical adsorption of the polymer onto the surface of the support member and at least one other domain that is chemically reactive to allow covalent cross-linking with a suitable cross-linking agent; a suitable cross-linking agent; and a bioactive species. Alternatively, cross-linking is accomplished through the non-covalent means listed above.

Optionally, additional layers of hydrophilic material can be attached to the first layer. Preferably, the hydrophilic material is comprised of one or more hydrophilic surfactants, homopolymers, or copolymers that contain chemically functional groups capable of reacting with unreacted cross-linking groups from the first layer. It is also preferred that the hydrophilic material has additional chemically functional groups to provide increased hydrophilicity to the construction and for optional attachment of bioactive species thereto.

Suitable materials for a hydrophobic polymeric biodegradable support member include, but are not limited to, polyglycolide (PGA), copolymers of glycolide, glycolide/L-lactide copolymers (PGA/PLLA), lactide/trimethylene carbonate copolymers (PLA/TMC), glycolide/trimethylene carbonate copolymers (PGA/TMC), polylactides (PLA), stereo-copolymers of PLA, poly-L-lactide (PLLA), poly-DL-iactide (PDLLA), L-lactide/DL-lactide copolymers, copolymers of PLA, lactide/tetramethylglycolide copolymers, lactide/α-valerolactone copolymers, lactide/ε-caprolactone copolymers, hyaluronic acid and its derivatives, polydepsipeptides, PLA/polyethylene oxide copolymers, unsymmetrical 3,6-substituted poly-1,4-dioxane-2,5-diones, poly-β-hydroxybutyrate (PHBA), PHBA/bhydroxyvalerate copolymers (PHBA/HVA ), poly-p-dioxanone (PDS), poly-a-valerlactone, poly-e-caprolactone, methacrylate-N-vinyl-pyrrolidone copolymers, polyesteramides, polyesters of oxalic acid, polydihydropyranes, polyalkyl-2-cyanoacrylates, polyurethanes, polyvinylalcohol, polypeptides, poly-B-malic acid (PMLA), poly-B-alcanoic acids, polybutylene oxalate, polyethylene adipate, polyethylene carbonate, polybutylene carbonate, and other polyesters containing silyl ethers, acetals, or ketals, alginates, and blends or other combinations of the aforementioned polymers. In addition to the aforementioned aliphatic link polymers, other aliphatic polyesters may also be appropriate for producing aromatic/aliphatic polyester copolymers. These include aliphatic polyesters selected from the group of oxalates, malonates, succinates, glutarates, adipates, pimelates, suberates, azelates, sebacates, nonanedioates, glycolates, and mixtures thereof. These materials are of particular interest as biodegradable support membranes in applications requiring temporary support during tissue or organ regeneration. A preferred material for use as a biodegradable support member is poly(glycolic acid).

To construct the present invention, a first layer is formed on a support member by adsorbing a polymeric surfactant to the surfaces of the support member followed by cross-linking the surfactant to itself. For a porous support member, the first layer is optionally adsorbed to a material defining the porous void spaces of the support member as well. For example, a solution comprised of a polymeric surfactant, such as poly(vinyl alcohol), is dissolved in a suitable solvent at a concentration of about 0.001% to about 99.9%, preferably about 0.01% to about 50%, more preferably about 1.0% to about 25%, and most preferably about 0.25% to about 5% and initially adsorbed onto the surfaces and optionally into the porous spaces of a porous support member simply by dipping the support member in the solution for about 0.05 minutes to about 20 minutes to permit physisorption of the suriactant to the surfaces of the support member. Suitable materials for the first layer include, but are not limited to, polyvinyl alcohol, polyethylene glycol, polypropylene glycol, dextran, agarose, alginate, polyacrylamide, polyglycidol, polyvinyl alcohol-co-polyethylene, poly(aspartic acid), poly(ethyleneglycol-co-propyleneglycol), poly(vinyl acetate-co-vinyl alcohol), polyacrylic acid, poly-B-malic acid), polyamide, polylysine, polyethyleneimine, polyvinyl pyrrolidone, and polysaccharides, or their copolymers, either alone or in combination. Preferably, the polymer that forms the first layer contains chemically functional side groups on each monomei unit and is biodegradable by hydrolysis or enzymatic cleavage of the polymer backbone. If the polymer that forms the first layer is not biodegradable by hydrolysis or by enzymatic degradation in vivo, but is below about 70,000 g/mol molecular weight, preferably below about 45,000 g/mol molecular weight, more preferably less than about 10,000 g/mol, and linked by cross-links that are reversible or biodegradable, then these components of the first layer can usually be removed from the body of the recipient through the kidneys (Park, K., Shalaby, W. S. W., Park, H., Eds., *Biodegradable Hydrogels for Drug Delivery*, Technomic Publishing Company, Inc., Lancaster, Pa., pp. 236–237 (1993)).

If copolymers are used to form the first layer, preferred copolymers for formation of the first layer are copolymers comprised of at least one moiety capable of physicochemically adsorbing to the support member, a moiety capable of chemical modification with a suitable agent, and a moiety capable of interacting with high surface tension fluids. These moieties may be selected such that one moiety fulfills all of these three roles simultaneously, fulfills two roles, or fulfills only one role.

Suitable solvents for the hydrophilic polymers of the first layer include, but are not limited to, methanol, ethanol, isopropanol, tetrahydrofuran, trifluoroacetic acid, acetone, water, dimethyl formamide (DMF), dimethyl sulfoxide (DMSO), acetonitrile, benzene, hexane, chloroform, methylene chloride, supercritical carbon dioxide, or other compounds which solvate the first layer.

If the polymer chosen for the first layer dissolves in only high surface tension solvents, the biodegradable support member should be prewetted with a miscible solvent having a low surface tension to effect adsorption of the polymer for the first layer. For porous biodegradable support members, excess adsorbed surfactant may be rinsed from the surface of the support member using fresh solvent to prevent bulk-deposited surfactant from partially blocking pores of the support member. Though optional, this step is preferred in order to ensure that the pores of a porous biodegradable support material are not obstructed with surfactant.

The polymeric surfactant of the first layer is cross-linked to itself using a suitable cross-linking agent to produce surface-bound planar molecules of extremely high molecular weight. These very high molecular weight molecules serve to greatly reduce or eliminate the potential for desorption or migration of the surfactant. The cross-linked polymeric surfactant initially provides a stable layer of material to which bioactive species are subsequently immobilized. A key feature of the present invention is the biodegradability of the cross-linked first layer.

When a polymeric surfactant of the present invention is cross-linked together with covalent bonds, the covalent bonds must be cleavable under appropriate conditions in order to be biodegradable. These conditions include in vivo conditions, conditions that simulate in vivo conditions, and exposure to enzymes or other hydrolytic conditions in vitro. The cross-linkages that connect the components of the first layer together are broken down in vivo by either enzymatic or non-enzymatic hydrolysis. The cross-linkages must be broken down in order for the first layer to be removed from the body of the recipient through normal physiological processes. In vitro simulation of in vivo conditions may include constant replenishing of an aqueous environment, the use of mechanical stresses to simulate load-bearing situations, or the use of proteolytic or non-proteolytic enzymes to enhance the break-down of the cross-links, for example.

Suitable reagents for forming cleavable covalent cross-linkages between polymer repeat units, or mers, of a polymeric surfactant attached to a biodegradable support member are compounds comprised of at least two chemically functional groups, either homofunctional or heterofunctional, that include, but are not limited to, aldehydes, epoxides, acyl halides, alkyl halides, isocyanates, amines, anhydrides, acids, alcohols, haloacetals, aryl carbonates, thiols, esters, imides, vinyls, azides, nitros, peroxides, sulfones, and maleimides, dissolved in solvents that wet the adsorbed layer. In addition, vinyl sulfone, succinyl chloride, polyanhydrides, poly-B-malic acid), ethylene glycolbis-[succinimidyl succinate], succinimidyl succinate-polyethylene glycol, and succinimidyl succinamide-polyethylene glycol can also be used as cross-linking agents.

Solvents suitable for dissolving the cross-linking reagent include, but are not limited to, acetone, water, alcohols, tetrahydrofuran (THF), dimethyl sulfoxide (DMSO), dimethyl formamide (DMF), benzene, acetonitrile, and dioxane. Other cross-linking reagents include, but are not limited to, free radicals, anions, cations, plasma irradiation, electron irradiation, and photon irradiation. One preferred cross-linking agent is ethylene glycolbis-[succinimidylsuccinate]. A preferred reaction scheme for immobilizing functional groups onto a biodegradable support is to cross-link polylysine with ethylene glycolbis-[succinimidylsuccinate] to form hydrolyzable ester bonds.

Regardless of which cross-linking agent is used, the cross-linking agent is optionally added in excess, i.e, in such an amount that sufficient unreacted chemically functional groups of the cross-linking reagent will be present to serve as points of attachment for the bioactive species or an optional second layer of hydrophilic polymers following the cross-linking step. Thus, the cross-linking scheme fulfills two roles. In one role, cross-linking forms surface-bound planar molecules of extremely high molecular weight having covalent bonds connecting the molecules that are cleavable under the above-described appropriate conditions. In another role, cross-linking provides chemically functional groups to which the bioactive species or an optional second layer is subsequently attached. The degree of cross-linking can vary from about 5% to about 100%. This provides a range of biodegradation rates for the first layer.

In an alternative embodiment, the polymeric surfactant of the first layer can be cross-linked on a biodegradable support member with methods that do not form covalent bonds between the components of the polymeric surfactant. For example, polymeric surfactants containing numerous nitrile groups can spontaneously self assemble into a stable conformal coating when adsorbed onto a biodegradable support member. The stability of the coating is derived from the physical cross-linking of neighboring polymer chains via cyano polar interactions.

In another embodiment, the polymeric surfactant may be non-covalently cross-linked using a suitable agent via acid-base coacervation, e.g., a first layer formed of a cationic polymeric surfactant can be physically cross-linked by the application of an anionic agent. In addition, an amphoteric polymeric surfactant may spontaneously self assemble into a conformal coating via internal acid-base coacervation.

Other non-covalent cross-linking chemistries include, but are not limited to, carboxylic acid-ether complexation, ion complexation, ionic interactions, metal complexation, and alcoholic hydrogen bonding, for example. Carboxylic acid-ether complexation can be performed as follows: poly (acrylic acid) can be adsorbed onto a biodegradable support, followed by a layer of poly(ethylene glycol). The oxygens within the ether backbone of PEG will form a hydrogen bond complex with the carboxylic acid functionalities of the poly(acrylic acid) backbone. ion complexation can be accomplished using multivalent elements such as metals or boron. For example, by adding sodium borax ($Na_2B_4O_7$) to PVA, each boron atom will form an ionic charge complex with four ionized oxygens from the free hydroxyl groups. Ionic interactions between anionic and cationic entities can produce transiently stable bonds. Alcoholic hydrogen bonding can be accomplished, for example, by repeatedly freezing and thawing PVA.

The degree of covalent cross-linking of the first layer may be assessed by Fourier Transform Infrared Spectroscopy (FTIR). For example, with FTIR, the free hydroxyl groups of poly(vinyl alcohol) (PVA) are detectable before cross-linking at approximately 3349 $cm^{-1}$. After cross-linking, the peak shifts to approximately 3383 cm$^{-1}$ and decreases in intensity. As a positive internal control, the peak at approximately 2942 cm$^{-1}$ due to the $CH_2$ groups does not change position or intensity as a result of cross-linking. Thus, a shift in the hydroxyl group (OH) peak position from approximately 3349 cm$^{-1}$ to approximately 3383 cm$^{-1}$ with a decrease in peak intensity is indicative of the degree of cross-linking of the first layer. In the case of degradable polymers in which the underlying support contains oxygen, more surface-sensitive techniques as attenuated total reflectance (ATR) FTIR would be expected to demonstrate the presence of hydroxyl groups before and after crosslinking.

The addition of a first or second layer of poly(lysine) onto a poly(glycolic acid) (PGA) support or a PVA-cbated PGA support member may be detected by X-ray photoelectron spectroscopy (XPS). The addition of amino groups ($NH_2$) onto the surface can be detected by the measurement of nitrogen. Nitrogen is not present in either PGA or PVA. Similarly, the addition of cell adhesion peptides such as the Arg-Gly-Asp amino acid sequence onto a support of PGA or PLA using PVA as the first layer to which the peptides are attached can be detected by XPS or elemental analysis.

In the case of a three-dimensional device, such as a foam or sponge, the presence of poly(lysine) or cell adhesion peptides attached in the bulk to PVA on a PGA support member is preferably detected by elemental analysis.

The presence of amine-containing first or second layers on a PGA support can be detected using colorimetric assays, with dyes such as ninhydrin, Ponceau S stain or sulfo-SDTB.

The presence of first or second layers containing amino groups or hydroxyl groups can also be detected using static SIMS, which detects molecular groups.

Figure 5:
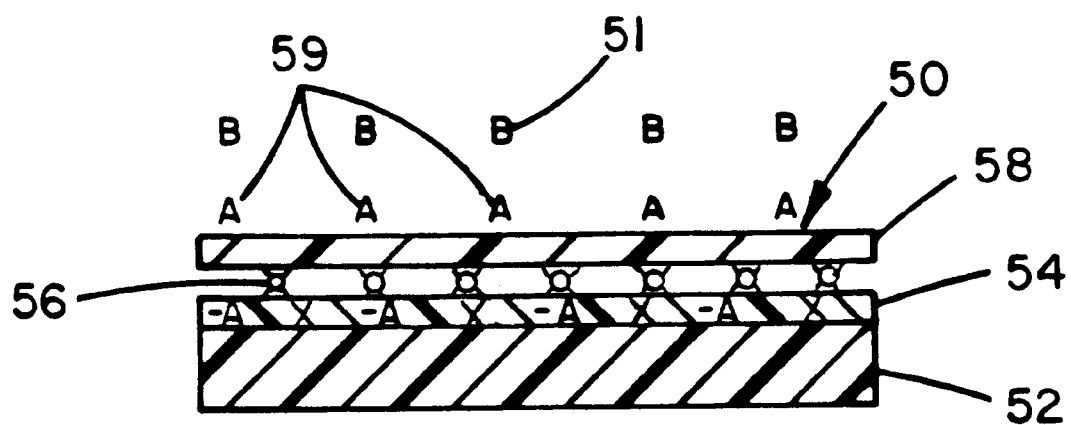
FIG. 5 illustrates a cross-section of the present invention (50) wherein a first layer (54) is attached to a support member (52) such that the number of chemically functional groups available for immobilizing bioactive species (51) from the first layer is increased by the addition of a second layer (58). The letter "x" indicates that the constituents of the first-layer are cross-linked together. The symbol ¤ (56) represents excess chemically functional groups of the cross-linking agent. The symbol "–A" in the region depicting the first layer indicates chemically functional groups of the constituents of the first layer that have been consumed during the formation of the first layer and are no longer available for immobilization of bioactive species. The letter "A" (59) on the second layer represents unreacted chemically functional groups of the constituents of the second layer that are available for immobilization of bioactive species or attachment of additional layers of hydrophilic materials thereto.
Figure 6:
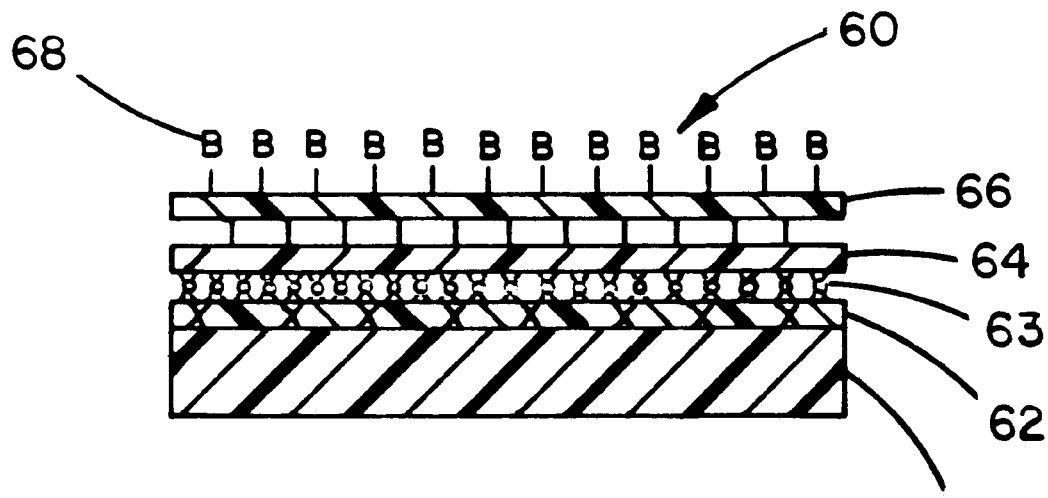
FIG. 6 illustrates a cross-section of the present invention (60) having a first layer (62) attached to a support member (61) with a second layer (64) attached to the first layer. The letter "x" indicates that the constituents of the first layer are cross-linked together and the symbol ¤ (63) indicates excess chemically functional groups of the cross-linking agent to which a second layer (64) is attached. An additional layer (66) of hydrophilic polymers is attached to the second layer with bioactive species (68) immobilized to the additional layer. The additional layer of hydrophilic polymers is represented as being attached to the second layer by a plurality of vertical lines.

The composition of the optional second layer of hydrophilic polymers is chosen both for the ability of the second layer to cooperate with the first layer to promote wetting of the hydrophobic support member with high surface tension fluids.and for its ability to provide a variety of chemically functional groups not present on the first layer to which bioactive species can be immobilized. It is understood that additional layers of hydrophilic polymers can be attached to the second layer to form a plurality of layers of hydrophilic polymers on the support member (see FIG. 6, for example). When forming an additional layer, various hydrophilic polymers may be selected for use in making the layer. Different hydrophilic polymers provide a variety of chemically functional groups to select from when attaching bioactive species to the second layer or to an additional layer (see FIG. 5). As a result, the chemically functional groups of the second layer dictate the type and number of functional groups available for immobilization of bioactive species thereto. Furthermore, attachment of a second layer onto the unconsumed moieties of the cross-linking agent amplifies the number of chemically functional groups available for the immobilization of bioactive species to numbers much greater than would be possible using only the first layer of material on the support member.

Figure 3:
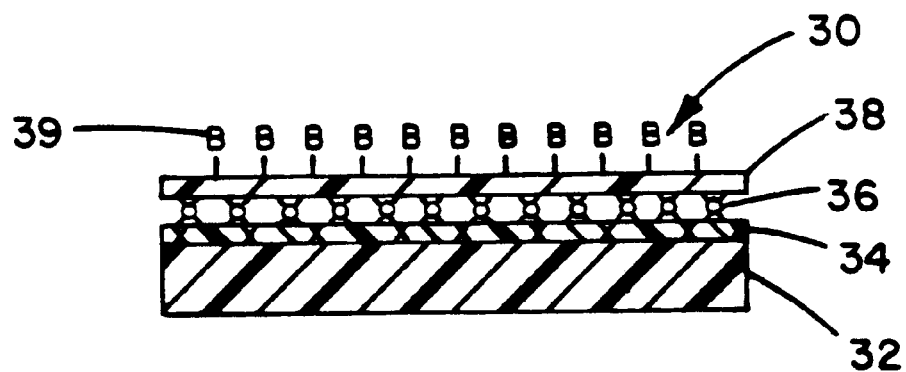
FIG. 3 illustrates a cross-section of the present invention (30) having a first layer (34) attached to a support member (32) with a second layer (38) of hydrophilic polymers attached to the first layer and bioactive species (39) immobilized to the second layer. The letter "x" indicates that the constituents of the first layer are cross-linked together and the symbol ¤ (36) indicates excess chemically functional groups of the cross-linking agent to which the second layer is attached.
Figure 4A:
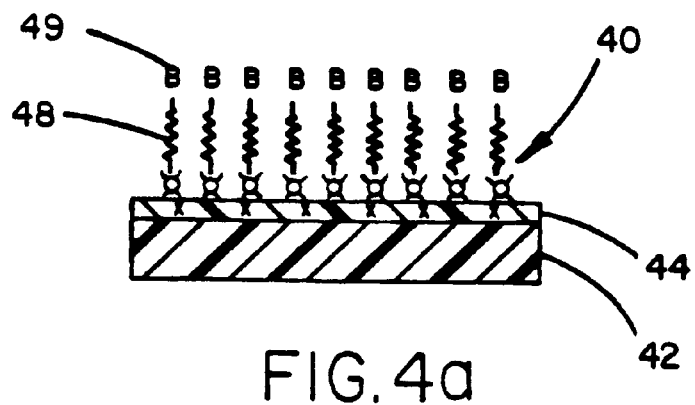
FIG. 4a illustrates a cross-section of the present invention (40) having a first layer (44) attached to a support member (42) wherein a spacer compound (48) is interposed between the first layer and a bioactive species (49). The letter "x" indicates that the constituents of the first layer are cross-linked together. The symbol ¤ represents excess chemically functional groups of the cross-linking agent through which the spacer compound is attached.
Figure 4B:
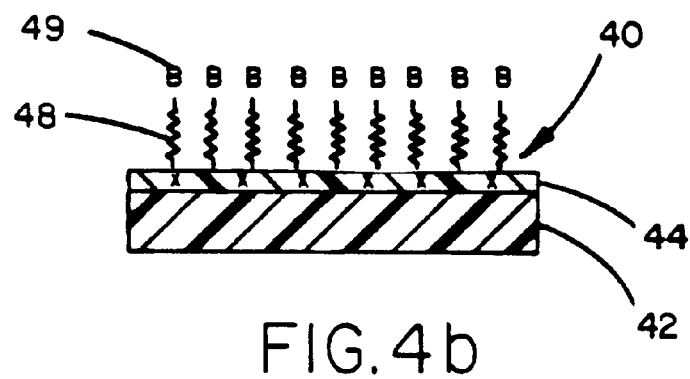
FIG. 4b illustrates a cross-section of the present invention (40) having a first layer (44) attached to a support member (42) wherein a spacer compound (48) is interposed between the first layer and a bioactive species (49). The letter "x" indicates that the constituents of the first layer are cross-linked together. The spacer compound is attached to the first layer through chemically functional groups of the first layer.
Figure 4C:
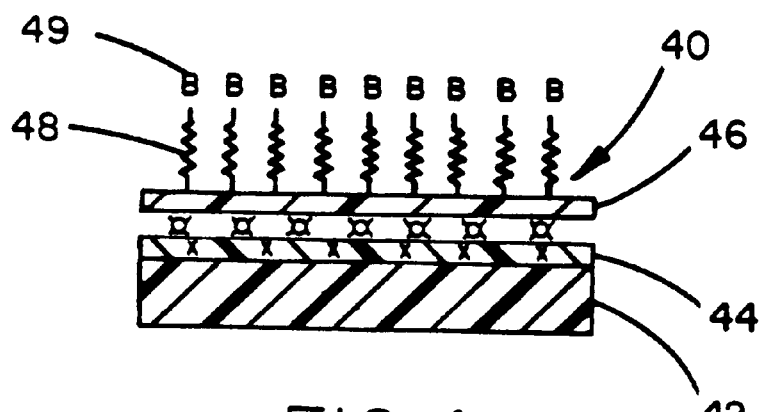
FIG. 4c illustrates a cross-section of the present invention (40) having a first layer (44) attached to a support member (42) with a second layer (46) of hydrophilic polymers attached to the first layer through excess chemically functional groups represented by the symbol ¤ spacer compound (48) is attached to the second layer and bioactive species (49) attached to the spacer compound.

A second layer is formed on the first layer by attaching a hydrophilic polymer to the cross-linked polymeric surfactant of the first layer through unreacted chemically functional groups of the cross-linking reagent (see FIG. 3) or through unreacted chemically functional groups of the cross-linked polymeric surfactant. Preferably, the hydrophilic polymers are covalently attached to chemically functional groups of the first layer. In one method, the second layer is attached to the first layer by immersing a biodegradable support member, having an adsorbed and cross-linked first layer, into a solution of a hydrophilic polymer of the second layer at a concentration of about 0.001% to about 99.9%, preferably about 0.01% to about 50%, more preferably about 1.0% to about 25%, and most preferably about 0.25% to about 5%. The solution of hydrophilic polymer may include an appropriate catalyst, such as organic acids or bases, mineral acids or bases, Lewis acids or bases, organometallic catalysts, organic and/or inorganic salts, heat, pressure, electron irradiation, photon irradiation, plasma irradiation, corona discharge, or pH, to effect attachment to the chemically functional groups of the first layer. Suitable hydrophilic polymers for use in forming the second layer include, but are not limited to, polyvinyl alcohol, polylysine, polyacrylic acid, polyvinylpyrrolidone, polyethylene glycol, alginate, sepharose, agarose, polyethyleneimine, polyallylamine, polyornithine, poly-(B-malic acid), polysulfone, or their copolymers, either alone or in combination. Polylysine is preferred. Suitable solvents for dissolving the hydrophilic polymers include, but are not limited to, water, alcohols, acetone, dioxane, dimethylformamide, tetrahydrofuran, and acetonitrile, etc.

Once the first and optional second layer of hydrophilic material is formed on a biodegradable support member, bioactive species are immobilized thereon using mild bioconjugation techniques known to those skilled in the art (See K. Mosbach, *Immobilized Enzymes and Cells*, Part B, Academic Press (Orlando, Fla.), (1987); G. T. Hermanson, A. K. Mallia, P. K. Smith, "Immobilized Affinity Ligand Techniques," *Academic Press*, San Diego, (1992); and S. F. Karel, S. B. Libicki, C. R. Robertson, "The Immobilization of Whole Cells: Engineering Principles," *Chemical Eng. Sci.*, 40: 1321 (1985), for example). Mild bioconjugation schemes are preferred for immobilization of bioactive species in order to eliminate or minimize damage to the structure of the biodegradable support member, the polymeric surfactant of the first layer, the hydrophilic polymer of the optional second layer, and the bioactive species.

In addition to providing variability in the number and identity of chemically functional groups that can be used to immobilize bioactive species, variability in the number and identity of the functional groups of the optional second hydrophilic polymer layer can be used to increase the wetability of the biodegradable support member with high surface tension fluids. In one embodiment, a porous hydrophobic biodegradable support member is modified only at its surface by a thin first and second layer, leaving the material defining the porous void spaces of the support member unmodified and hydrophobic. In another embodiment, the first and second layers can also be formed on the material defining the interior porous void spaces of the porous biodegradable support member and bioactive species can be immobilized thereon. In this embodiment, a continuous water phase through the pores of the biodegradable support member can be readily established and maintained, resulting in good transport of reaction products or nutrients, for example, across the porous support member. Thin coatings are particularly preferred for porous biodegradable support members because the thin coatings do not appreciably decrease the porosity of the support member.

In some circumstances, the interaction of a solution-phase reactant with an immobilized bioactive species may be suboptimal. For example, steric hindrances between the first layer and the immobilized bioactive species may limit the approach of the solution phase reactant to the bioactive species. In addition, physical bulk, electrostatic repulsion, or inappropriate positioning of the bioactive species may also contribute to reduced efficiency of the immobilized bioactive species. Accordingly, it may be desirable to place one or more additional compounds as a "spacer" or "tether" between the chemically functional groups of the first layer or optional second layer and the bioactive species to increase the space between the layer and the bioactive species. Suitable compounds for use as a spacer include, but are not limited to, ethylene glycolbis-[succinimidylsuccinate], succinic acid, diaminohexane, glyoxylic acid, short chain polyethylene glycol, and glycine, for example. It is understood that the optional second layer may itself serve as a spacer arm without necessitating the use of a separate spacer compound or that excess chemically functional groups of the cross-linking agent may also serve as a spacer compound.

The covalent immobilization of bioactive species onto support members according to the present invention is generally reversible, i.e., the bioactive species are released from the first or optional second layer of the biodegradable support member in a controlled, or predictable, manner over time. In addition, spacers, or tethers, capable of selectively releasing immobilized bioactive species provide another degree of controlled release of bioactive species. These constructions have utility in receptor/ligand interactions, molecular identification and characterization of antibody/antigen complexes, and selective purification of cell subpopulations, etc.

Selective release of the bioactive species is performed by cleaving the spacer compound under reaction conditions including, but not limited to, photon irradiation, enzymatic degradation, decomplexation, acid-base neutralization, hydrogen-bond disruption, oxidation/reduction, or hydrolysis, for example. The selective cleavage and release of immobilized bioactive species may be accomplished using techniques known to those skilled in the art (see for example, H. R. Horton & H. E. Swaisgood, "Covalent immobilization of proteins by techniques which permit subsequent release,"*Meth. Enzymology,* 135: 130 (1987); S. S. Wong, Chemistry of Protein Conjugation and Cross-Linking, CRC Press (1991); and U.S. Pat. No. 4,745,160, issued to Churchill et al., which is incorporated herein by reference). Suitable compounds for use as cleavable tethers, or cleavable spacers, include, but are not limited to, polyhydroxyacids, polyanhydrides, polyamino acids, tartarates, and cysteine-linkers such as Lomant's Reagent, for example.

The present invention is not limited to the above-described embodiments having a first layer and an optional second layer. In other embodiments, additional layers of hydrophilic polymers may be attached to existing layers on the support member to form constructions with multiple layers of hydrophilic material attached thereto.

Without intending to limit the scope of the present invention, the following examples illustrate how the present invention can be made and used.

EXAMPLES

Example 1

This example illustrates a method for forming a first layer of reversibly cross-linked polymeric surfactants on a poly (glycolic acid)-co-poly(lactic acid) (PGA:PLA) support member in the form of a PGA:PLA fiber mesh (e.g., Vicryl™ knitted mesh, Ethicon, Somerville, N.J., 90:10 PGA:PLA). The method is as follows. Two 2×2 cm pieces of Vicryl™ mesh were rinsed with isopropanol (IPA) for 30 seconds, then placed in a 0.5% aqueous solution of polylysine (0.053 g polylysine HCL, Aldrich, in 10 ml carbonate buffer 0.05M, pH 9.6, adjusted with NaOH) for 10 min. The polylysine solution was rinsed from the fibers by soaking the fiber mesh in carbonate buffer, pH 9.6 for 5 min. and then in dimethylsulfoxide (DMSO) for 5 min. The two pieces of fiber mesh were then placed in a solution of ethylene glycolbis-[succinimidylsuccinate] (0.10 g EGS, Pierce, in 15 ml of anhydrous DMSO, Aldrich) for 2 h. to cross-link the polylysine molecules, thus rendering them more stable. The fiber mesh was then rinsed twice with distilled water for 5 min. each time.

The fiber mesh was rinsed by soaking the mesh in isopropyl alcohol (IPA) for 30 seconds and then air-dried. The wettability of the fiber mesh was compared to an untreated fiber mesh by placing a small drop of water on the mesh while holding the mesh horizontally suspended in the air. The water droplet remained beaded up in a hemispherical shape on the untreated PGA:PLA mesh, whereas on the PGA:PLA mesh treated according to the present invention the water droplet immediately fell through the mesh.

A 5×5 mm portion of the mesh was stained with Ponceau S stain (Sigma, 0.04 g Ponceau S stain added to 575 ml concentrated acetic acid in 100 ml distilled water), demonstrating the presence of amino groups by the formation of a faint pink coloration on the mesh. A 1×1 cm segment of the mesh was used to measure the number of available amino groups on the mesh with the sulfo-SDTB assay (Pierce). See example 2 for results of the sulfo-SDTB assay.

Example 2

This example describes the amplification of the first layer of polylysine with a second layer of polylysine on the sample described in Example 1. One of the two PGA:PLA meshes of Example 1 was placed back in the 0.5% polylysine solution (before rinsing with distilled water or IPA) for 15 min. The sample was then rinsed for 5 min. in 20 ml of distilled water, rinsed with IPA for 30 sec. and allowed to air dry.

The wettability of the fiber mesh was compared to untreated fibers by placing a small drop of water on the mesh. The water droplet remained beaded up in a hemispherical shape on the untreated PGA:PLA mesh, whereas on the PGA:PLA mesh treated according to the present invention the water droplet immediately fell through the mesh.

A 5×5 mm section of the sample was stained with Ponceau S stain demonstrating a very uniform, dark pink coloration. Three 1×1 cm segments of the mesh with two layers of polylysine were analyzed by the sulfo-SDTB assay.

To conduct the sulfo-SDTB assay, a stock solution was prepared by dissolving 10.6 mg of sulfo-SDTB and 0.444 ml DMF in 3.55 ml sodium bicarbonate solution. A standard curve was prepared by mixing 0.02 ml stock solution with 2 ml of 35% perchloric acid. Seven 1:2 dilutions were prepared from this initial solution and measured at 498 nm on a UV/Vis spectrophotometer to construct a calibration curve. The samples were soaked in 0.25 ml of stock solution for 10 min. The pieces were then rinsed with 4 ml of distilled water twice for 5 min. each rinse. Each piece was then placed in 2 ml of 35% perchloric acid for 10 min. One ml of perchloric acid solution from each of the pieces was measured on the UVNis spectrophotometer at 498 nm against a blank perchloric acid solution. The results were converted to units of nmol/$cm^2$ using the calibration curve equation. The difference in the number of amino groups between the first and second layer indicates the effect of amplification. No difference in amino groups between the Vicryl control and the first layer may be due to the inability of the sulfo-SDTB reagents to access the low number of uncrosslinked amino groups, whereas the amino groups on the side chains of the polymer of the second layer were able to react with the free amino groups of the first layer.

| Membrane | [NH$_2$] (nmol/cm$^2$) |
|---|---|
| Vicryl (control) | 0.78 ± 0.02 |
| Vicryl + polylysine (single layer) | 0.82 ± 0.15 |
| Vicryl + polylysine + polylysine (2 layers) | 2.38 ± 0.18 |

Example 3

This example describes the treatment of a thin film support member comprised of poly(d,l-lactic acid):poly (glycolic acid) (d,l-PLA:PGA) copolymer of the ratio 85:15 PLA to PGA (Birmingham Polymers, Birmingham, Ala.) with a layer of polyethyleneimine (PEI, Sigma) to render it more water wettable and to incorporate functional groups onto the surface of the film.

In the method, a PLA:PGA 85:15 polymer film approximately 2 cm by 2 cm by 20 micrometers was cut from a larger film prepared by solvent casting the polymer from acetone using a draw-down solvent casting apparatus (BYK-Gardner, Silver Springs, Md. Model AG-3860). The polymer film was placed in isopropanol for 0.5 min. Excess isopropanol was removed by shaking off the excess, but not allowing the film to completely dry. The film was placed in an aqueous solution of 0.5% PEI (in carbonate buffer, pH 9.6) for 10 min., rinsed for 5 min. in carbonate buffer, then rinsed in distilled water, and placed in a solution of 1% glutaraldehyde in carbonate buffer for 20 min. to form hydrolytically labile Schiff base (imine) linkages. The sample was rinsed twice for 5 min. each in distilled water, then dried by wetting the sample in isopropanol for 30 sec. and air-dried.

Droplets of water were placed on the material and measured using a goniometer, demonstrating a decrease of approximately 10 degrees in the contact angle. A 5×5 mm portion of the film was stained with Ponceau S stain, demonstrating a faint pink coloration. Part of the sample was saved for analysis by sulfo-SDTB (see Example 4 for sulfo-SDTB results).

Example 4

A second layer of PEI (Sigma) was added to the first layer of a piece of the material made in Example 3 by immersing the sample in a 0.5% aqueous solution of PEI (before rinsing with IPA) for 30 min, then rinsing twice in distilled water for 5 min. each time. The sample was rinsed by immersing the sample in isopropanol for 30 sec. and then air-dried. A piece of the sample was stained by immersing it in Ponceau S stain. A dark pink coloration was observed. Three 1×1 cm pieces of the sample were analyzed by sulfo-SDTB assay. The results of the sulfo-SDTB analyses were:

| Membrane | [NH$_2$] (nmol/cm$^2$) |
|---|---|
| PLA:PGA (control) | 0.06 ± 0.05 |
| PLA:PGA + PEI (single layer) | 0.53 ± 0.20 |
| PLA:PGA + PEI + PEI (2 layers) | 0.81 ± 0.06 |

Example 5

This example describes a method to add a second layer of polyethyleneimine to a first layer of polylysine on a PGA:PLA (Vicryl™) porous fiber mesh support. The sample was placed in isopropanol for 30 sec., then placed into a 0.4% solution of polylysine (0.04 g polylysine hydrochloride, Aldrich, in 10 ml carbonate buffer, pH 9.6) for 10 min. The sample was then rinsed in carbonate buffer for 5 min., followed by a rinse in acetone for 5 min. The sample was then placed into a solution of 0.4% ethylene glycolbis-[succinimidylsuccinate] solution (0.057 g EGS, Pierce, in 15 ml acetone, Aldrich) for 2 h. The sample was rinsed in 20 ml of distilled water for 20 min., then the sample was rinsed by soaking in isopropanol for 30 sec. and a 5×5 mm portion was air-dried. The dried portion of the sample was stained with Ponceau S stain which demonstrated a uniform pink coloration.

To amplify the coating, the remaining portion of the sample was placed immediately into a 0.5% PEI solution for 15 min before rinsing with distilled water or IPA. The sample was rinsed twice with distilled water for 5 min. each rinse, then rinsed with isopropanol for 30 seconds and air-dried. A 5×5 mm piece of the sample was stained with Ponceau S stain, demonstrating a dark pink coloration. Sulfo-SDTB analysis of the available amino groups produced the following results:

| Membrane | [NH$_2$] (nmol/cm$^2$) |
|---|---|
| Vicryl (control) | 0.46 ± 0.08 |
| Vicryl + polylysine (single layer) | 3.16 ± 1.57 |
| Vicryl + polylysine + PEI (2 layers) | 5.01 ± 0.40 |

Example 6

This example describes the treatment of a PLA:PGA nonporous film with a first layer of PEI and a second layer of polylysine. A film of 85:15 PLA:PGA (Birmingham Polymers) was rinsed in IPA for 30 sec. and then placed in a 0.5% solution of PEI for 10 min. The sample was rinsed with carbonate buffer twice (5 min. each rinse) and then placed into a 1% glutaraldehyde solution in carbonate buffer for 20 min. The sample was then rinsed twice with distilled water (5 min. each rinse). Part of a portion of the sample was rinsed in IPA for 30 sec., air-dried, and stained with the Ponceau S stain, resulting in a faint pink coloration. Another part of the sample was analyzed by sulfo-SDTB. The rest of the sample was placed in a 0.4% solution of polylysine in carbonate buffer for 30 min to amplify the amino groups. The amplified sample was rinsed twice in distilled water (5 min. each rinse), rinsed in IPA for 30 sec. and air-dried. A portion of the amplified sample was soaked in Ponceau S stain demonstrating a medium pink coloration. A portion of the amplified sample was analyzed by sulfo-SDTB. The sulfo-SDTB results were:

| Membrane | [NH$_2$] (nmol/cm$^2$) |
|---|---|
| PLA:PGA (control) | 0.40 ± 0.27 |
| PLA:PGA + PEI (single layer) | 0.93 ± 0.12 |
| PLA:PGA + PEI + polylysine (2 layers) | 1.13 ± 0.06 |

Example 7

This example describes a method to ascertain the stability of the coating on a PGA:PLA scaffold. A 2 cm×2 cm sample of 90:10 PGA:PLA fiber mesh (Vicryl™) was wetted out with IPA for 30 sec., soaked in 10 ml of 0.5% polylysine in carbonate buffer for 10 min., rinsed in 20 ml carbonate buffer (0.05M, pH 9.6) for 3 min. and placed into 15 ml of a 1% glutaraldehyde solution in carbonate buffer (0.05M, pH 9.6) for 20 min. The sample was removed, rinsed twice with distilled water, a portion removed for Ponceau S staining, and the rest returned to the 0.5% polylysine solution for 4 h, thus producing two layers of polylysine on the sample. The sample was then rinsed in 20 ml distilled water twice (5 min. each rinse), rinsed for 30 sec. in IPA and air-dried.

A portion of the sample was removed for Ponceau S staining, which demonstrated a uniform red coloration, indicating the presence of amino groups. The sample was placed in 15 ml of phosphate buffered saline (Dulbecco's PBS, pH 7.2,Gibco/BRL) at 37° C. for one week. Each day, the sample was placed in fresh buffer and a portion was removed and stained with Ponceau S stain. The results demonstrated that the coating remained intact for 7 days as indicated by a visual comparison of the uniform red coloration of all the samples. Untreated controls demonstrated no coloration.

Example 8

This example demonstrates a comparison of treated and untreated samples for assessment of cell toxicity. In a sterile laminar flow hood, a package of PGA:PLA fiber mesh (Vicryl™) was opened, a 5×5 cm piece was cut and placed in a sterile container as a control. Another 5×5 cm piece was cut and coated with PEI according to the following protocol (conducted entirely in the sterile hood, all beakers and utensils were autoclaved prior to use). The mesh was placed in 40 ml of IPA for 30 sec., soaked in 20 ml of a 0.5% sterile filtered PEI solution in carbonate buffer for 10 min., rinsed in 60 ml of carbonate buffer for 5 min., rinsed in 25 ml of acetone for 3 min., then added to an EGS solution (0.202 g EGS in 30 ml acetone) for 2 h. with stirring. After 2 h., the sample was placed in the original PEI solution for 15 min. to amplify the coating, then the sample was rinsed with 60 ml sterile water for 5 min. twice.

A 5×5 mm portion was removed and stained with Ponceau S stain to confirm the attachment of amino groups. The rest of the sample was rinsed with IPA for 30 sec., air-dried and placed in a sterile container before removing the sample from the laminar flow hood. The Ponceau S stain demonstrated a uniform red coloration, indicating the presence of transiently immobilized amino groups.

The sterile control and treated samples were tested according to USP guidelines for cell toxicity using the Elution Test. The samples were placed in separate containers of minimal essential media (REM) for 24 hrs at 37° C. at a ratio of 30 m² per 5 ml. An aliquot of 2 ml of the MEM was then placed on a growing culture of L929 cells for 48 hrs at 37° C. After 48 hrs. the cells were analyzed for cell lysis and the presence of discrete intracytoplasmic granules. Results indicated that the untreated control and the treated test sample were both nontoxic. Positive (toxic) and negative (MEM alone) controls were used to assure the validity of the test.

Example 9

This example describes a method to measure the biocompatibility of a biodegradable sample modified by the attachment of a hydrophilic surfactant to provide increased wettability and chemically functional groups. The materials that can be used in this test method are those described in Examples 1 to 6. Samples of each of the test materials are sterilized by exposure to gamma irradiation at less than 4 mRad. The samples are implanted into rats. Tissue explants are examined by histological methods to detect abnormalities in tissue response. No differences are expected to be seen histologically between the treated and non-treated materials.

Example 10

This example describes a method to grow cartilage for reconstructive surgery. Human chondrocytes are harvested from a patient. The cells are cultured to increase the number of cells. The cells are collected and seeded onto a construct made from a poly(glycolic acid) mesh coated with reversibly cross-linked polylysine. The construct and the cells are incubated for 2 weeks at 37° C. in a humidified environment. The construct and cells are implanted into the defect area. The degradation of the polymer occurs simultaneously with the formation of a new extracellular matrix by the cells. Functional cartilage is expected to be formed.

Example 11

This example describes the determination of the degradation rate of a polymer construct by accelerated aging. Control samples were untreated PGA:PLA mesh (Vicryl™). The test samples were prepared in the following manner: 2.5 cm×2.5 cm samples of PGA:PLA mesh (Vicryl#) were soaked in 60 ml of IPA for 30 sec. and then placed in 135 ml of 0.5% PEI solution for 10 min. The samples were rinsed with 150 ml of carbonate buffer (pH 9.7) for 5 min., rinsed with 150 ml of acetone for 3 min. and then placed in a solution of EGS in acetone (1.024 g of EGS, Pierce, in 150 ml of acetone) under nitrogen for 2 hr. The samples were then transferred to 135 ml of a 0.5% PEI solution for 15 min. to amplify the coating. The molecular weight of a representative sample was measured at time 0 by determining the inherent viscosity (I.V.) of the material dissolved in hexafluoroisopropanol (HFIP). Samples were placed in phosphate buffered saline, pH 7.2 at 57° C. Twice each day for the duration of the study, the buffer was removed from each sample and replaced by fresh buffer. Samples were collected twice each day by removing the buffer and allowing the remaining pieces of polymer to dry. The collected samples were analyzed for molecular weight loss by inherent viscosity in HFIP. Results indicated an approximately equal loss in molecular weight for the treated samples as for untreated controls.

| Time (hours) | Untreated I.V. (dl/g) | Treated I.V. (dl/g) |
|---|---|---|
| 0 | 1.29 | 1.22 |
| 16 | 0.80 | 0.86 |
| 24 | 0.61 | 0.61 |
| 40 | 0.43 | 0.37 |
| 48 | 0.28 | 0.32 |
| 64 | 0.17 | 0.23 |
| 72 | 0.11 | 0.15 |

Example 12

This example describes a method to determine the long-term in vivo biocompatibility of a sample such as the one described in Example 8. This method is designed to determine the chronic response to the material. A sample is prepared according to Example 8, sterilized by gamma irradiation and inserted aseptically under the skin of rabbits. After 1 month, 2 months, and 4 months, samples are removed along tissues and inspected histologically to determine the response of the body to the device. No long-term adverse effects are expected.

Example 13

This example describes a method to deliver biologically active agents using the devices of the present invention. As a result of the treatment described in Example 5, the PGA fiber mesh is coated with reversibly cross-linked polylysine and PEI molecules, which impart greater hydrophilicity to the polymer and provide some free amino groups. Anti-inflammatory drugs are attached to the free hydroxyl groups using reversible cross-linking agents. The use of anti-inflammatory drugs is expected to decrease the extent of inflammation associated with the implantable device.

Example 14

This example describes a method to attach cell adhesion peptides to a device such as the ones described in Examples 1 and 3. The fiber mesh or solvent-cast film with a single layer is placed in a solution containing a cross-linking reagent. After 10 min. the sample is removed from the first solution and rinsed to remove excess cross-linking reagents. The sample is then placed in a solution containing cell adhesion peptides, which react with the cross-linking reagent attached to the polymer of the first layer. The presence of cell adhesion peptides is detected by an increase in cell spreading of endothelial cells in serum-free media. The use of cell adhesion peptides is expected to prolong attachment to the membrane of cells which are implanted with the device.

Example 15

This example describes an animal study to test the efficacy of a biologically active agent attached to the polymer scaffold. A membrane containing PLA:PGA solvent cast film and PGA fibers (e.g., Resolut® membrane, W.L. Gore & Associates, Inc., Flagstaff, Ariz.) is coated with reversibly cross-linked PEI. An anti-inflammatory agent is attached covalently to the free amino groups of the PEI. The samples are placed in the mandibula of a canine. Inflammation in the vicinity of test samples is compared to inflammation of control animals. The presence of anti-inflammatory drugs is expected to decrease the degree of inflammation at the implantation site.

Example 16

This example describes the use of the present invention to improve bone regeneration under a resorbable membrane in the treatment of periodontal disease. The use of a membrane has been shown to improve the regeneration of bone. The present example combines the use of a membrane with the release of a growth factor which stimulates new bone formation. Recombinant human bone morphogenetic protein (rhBMP-2) is attached to the free amino groups of PEI after reversibly cross-linking the PEI to a porous fiber portion of a membrane made from PGA fibers and a non-porous film of PLA:PGA (e.g., Resolut® membrane, W.L. Gore & Associates, Inc., Flagstaff, Ariz.). After 2, 4, 6, and 12 weeks the defect is probed to determine bone regeneration. The presence of rhBMP-2 is expected to increase the rate of bone formation compared to controls.

Example 17

This example describes the use of the present invention in the treatment of articular cartilage damage. The present invention in the form of a PGA fiber mesh treated with PEI and reversibly crosslinked with EGS is used to support autologous cartilage cells which are previously harvested and then seeded with the cells upon the fibers in an incubator to promote the formation of new cartilage. After 2 weeks, the construct is implanted into the articular cartilage defect. A degradable membrane is used to protect the construct from invasion by soft tissue cells. It is expected that functional articular cartilage will be formed.

Example 18

This example describes the use of the present invention as a surgical mesh. A PGA:PLA fiber mesh (e.g., Vicryl™ knitted mesh, Ethicon, Somerville, N.J.) is treated with PEI and crosslinked using EGS to form reversible cross-links. The antimicrobial drug gentamicin is attached to the free amino groups of the PEI. The mesh is placed on a surgical wound to control infection and prevent adhesion of two soft tissue types. The addition of the antimicrobial agent is expected to decrease the incidence of bacterial infections at the implantation site.

Example 19

This example describes the incorporation of drugs onto the surface of a device used as an anastomotic wrap to provide antiproliferative capability to the membrane. The PGA:PLA wrap (e.g. Vicryl™) is coated with PEI to provide functional sites for grafting of the antiproliferative drug to the membrane. Mycophenolic acid (Sigma) is attached through a carboxylic acid functionality to the free amino groups of the PEI with N,N'-Dicyclohexylcarbodiimide (IDCC, Pierce, Rockford, Ill.) in the following manner. The PEI-coated, PGA:PLA support is immersed in IPA for 30 sec. until it is completely wet. Next, the sample is immersed in a solution of 0.5 M mycophenolic acid in ethanol with stirring. A fixture is placed in the solution to keep the sample away from a stir bar. The solution is cooled to −10° C. Next, dicyclohexylcarbodiimide (0.5M in ethanol), also cooled to −10° C., is dropped into the stirring solution. The temperature is maintained at −10° C. until all of the DCC solution is added. The temperature is allowed to come to 40° C. slowly and the reaction continues overnight. Next, a few drops of acetic acid are added and the mixture stirs for 10 minutes more. The polymer is washed with fresh ethanol, water, and ethanol and desiccated. The PEI-coated PGA:PLA support is wrapped perianastomotically around arterial-vascular graft anastomoses to deliver pharmaceutical agents to prevent anastomotic hyperplasia. Drug is released from the copolymer wrap as the ester bonds between the drug and crosslinked PEI are hydrolyzed. The drug subsequently diffuses from the device. It is expected that the release of an antiproliferative compound as the membrane degrades will prevent the formation of hyperplasia associated with vascular grafts.

Example 20

This example describes an alternative method for reversibly stabilizing a first layer of PVA onto the degradable polymer support. A PGA:PLA mesh (e.g., Vicryl™) is rinsed with isopropanol for 0.5 min, then immersed in an aqueous solution of 1% PVA. Excess PVA is rinsed from the mesh in distilled water for 5 min., two times. The PGA mesh with PVA is placed in a solution of sodium tetraborate decahydrate ($Na_2B_4O_7 \cdot 10H_2O$) (Aldrich) at about pH 8. Each boron atom forms a non-covalent charge complex with four free hydroxyls. It is expected that the PVA layer increases the wettability of the mesh.

Example 21

This example describes an alternative method for reversibly stabilizing a first and second layer of a poly(anion) and a poly(cation) onto a biodegradable polymer support. A 2×2 cm sample of PGA:PLA fiber mesh (Vicryl™) support was rinsed with isoproponal for 30 sec., and placed in a solution of 2% poly(acrylic acid) (5.0 g 40 wt:wt% poly(acrylic acid):sodium salt, Aldrich, in 95 ml distilled water) for 15 min. The pH was adjusted to 2.5 using HCl. Excess poly (acrylic acid) was rinsed from the support with distilled water (1 min.) and the support was placed in a solution of 0.05% poly(lysine) (Aldrich) in distilled water for 20 h. The pH of the polylysine solution was adjusted to 7.0 with NaOH. The polylysine coacervated with the adsorbed poly (acrylic acid) to form a transiently cross-linked layer of poly(lysine). The wettability of the fiber mesh was compared to an untreated fiber mesh by placing a small drop of water on the mesh while holding the mesh horizontally suspended in the air. The water droplet remained beaded up in a hemispherical shape on the untreated PGA:PLA mesh, whereas on the PGA:PLA mesh treated according to the present invention the water immediately fell through the mesh, demonstrating an increase in hydrophilicity of the treated membrane compared to the untreated control.

Example 22

This example describes an alternative method for reversibly stabilizing a layer of poly(vinyl alcohol) (PVA) onto a degradable polymer support, comprising a method of freezing and thawing the PVA. In the method, a 2 cm×2 cm sample of PGA:PLA (Vicryl) was soaked in IPA for 30 sec., placed in a 1% aqueous solution of PVA (Spectrum) for 10 min. The support was then placed in a freezer at −20° C. After 6 hours, the sample was removed from the freezer and allowed to warm up to room temperature. After 6 hours, the sample was again placed in a freezer at −20° C. After 11 hours, the sample was again brought to room temperature. After 3 hrs, the sample was placed in distilled water for 5 min. twice. The sample was rinsed for 30 sec. in IPA and air-dried.

This process produced hydrogen bonds between the hydroxyl groups of the PVA. The wettability of the fiber mesh was compared to an untreated fiber mesh by placing a small drop of water on the mesh while holding the mesh horizontally suspended in the air. The water droplet remained beaded up in a hemispherical shape on the untreated PGA:PLA mesh, whereas on the PGA:PLA mesh treated according to the present invention the water soaked into the mesh, completely absorbing within 50 sec., demonstrating an increase in hydrophilicity of the treated membrane compared to the untreated control.

Example 23

This example describes a method for the detection of the degree of cross-linking of poly(vinyl alcohol) (PVA) on a biodegradable support member. Attenuated Total Reflectance Fourier Transform Infrared Spectroscopy (ATR-FTIR) is used to detect the free hydroxyl groups of the PVA before and after cross-linking as described in Example 22. A shift in the hydroxyl group (OH) peak position from approximately 3349 cm$^{-1}$ to approximately 3383 cm$^{-1}$ with a decrease in peak intensity is proportional to the degree of cross-linking. A decrease in the intensity of the peak of about 50% and a shift from approximately 3349 cm$^{-1}$ to approximately 3383 cm$^{-1}$ is expected when about 50% of the hydroxyl groups of the PVA are cross-linked.

Example 24

This example illustrates the present invention having a biodegradable support member comprised of a thin film of poly(lactic acid):poly(glycolic acid) (PLA:PGA) copolymer in a ratio of 85:15 PLA to PGA covering a metallic stent to form a composite. To construct the composite, a nitinol wire stent is covered with the PLA:PGA film support member. Once constructed, the composite device is immersed in isopropyl alcohol to prewet the support member. This is followed by immersion in an aqueous solution of about 1% polyethyleneimine (PEI) in acetone for about 5 min. followed by a washing in distilled water for about 10 min. to remove excess bulk copolymer. The adsorbed PEI is cross-linked according to that detailed in Example 3 to form a first layer on the support member component of the stent composite. A desired bioactive species, such as heparin, is then immobilized to the first layer. The presence of the bioactive agent is expected to decrease the incidence of thrombus associated with the device.

Example 25

This example describes the attachment of anti-adhesive compounds to resorbable materials to prevent early inflammatory events associated with foreign body reactions in vivo. Polyethylene glycol (PEG) is attached through available functional groups to PEI-coated PGA:PLA membranes. The presence of PEG molecules is expected to prevent the adsorption of proteins, which in turn is expected to prevent the attachment of cells to the membrane.

Example 26

This example describes the attachment of a protein to a resorbable scaffold to enhance the loading of the membrane over the loading of an untreated membrane. Bovine serum albumin (BSA) was chosen as a model protein for use in this example. BSA (Fraction V, Sigma) was labeled with $^{125}$I according to the following protocol: A 1.5 ml siliconized microcentrifuge tube (Fisher) was coated with Iodo-Gen (Pierce) reagent in advance by filling it with 200 µl of 20 µg/ml Iodo-Gen reagent and allowing it to dry overnight. The tube was stored at 4° C. until used. On the day of the iodination, the reaction tube was rinsed with PBS (Gibco/BRL), then 30 µg of BSA (7.5 µl of BSA at 4 mg/ml), 5 µl of Na $^{25}$I (1 mCi, Amersham), and 44 µl of PBS, pH 7.2 were added to the reaction vessel. The tube was gently agitated for 25 min., then the entire solution was transferred to a NAP-5 purification column (Pharmacia) which had been pre-equilibrated with PBS, pH 7.2. Ten 200 µl fractions were collected by gravity drip, adding 200 µl of eluent at a time and waiting until the column had stopped dripping before proceeding. In order to identify the fractions with iodinated protein, 1 µl from each fraction was added to 33 µl of BSA solution (10 mg/ml in PBS), to which was added 333 µl of a trichloroacetic acid (TCA) solution (100 µl/ml in distilled water). The samples were incubated for 1 h. at 4° C., forming a cloudy solution. The samples were centrifuged and the liquid fractions were transferred to a new tube and both solid and liquid fractions were measured for radioactivity. Significant radioactivity (>95%) in the solid fraction was found in samples 5, 6 and 7. The corresponding fractions were combined and stored at 4° C. until needed.

The support polymer samples were prepared in the following manner: two 2×2 cm pieces of PGA:PLA mesh (Vicryl™) were cut and placed in 30 ml of IPA for 30 sec., soaked in 10 ml of a 0.5% PEI solution in carbonate buffer, pH 9.6, for 10 min., rinsed in 30 ml of carbonate buffer for 5 min., rinsed in 10 ml of acetone for 3 min., then added to an EGS solution (0.122 g EGS in 15 ml acetone) for 2 hr. with stirring. After 2 hr., the samples were placed in the original PEI solution for 15 min. with stirring to amplify the coating, then the samples were rinsed with 30 ml distilled water for 5 min. twice. Finally, the samples were rinsed with 30 ml of IPA for 30 sec. and air dried. A 5×5 mm portion from each sample was removed and stained with Ponceau S stain to confirm the attachment of amino groups. The Ponceau S stain demonstrated a uniform red coloration, indicating the presence of transiently immobilized amino groups. One of the samples was cut into four 1×1 cm pieces, three of which were used to measure the concentration of amino groups by the sulfo-SDTB assay. The results were:

| Membrane | $[NH_2]$ (nmol/cm$^2$) |
| --- | --- |
| Vicryl (control) | 0.46 ± 0.08 |
| Vicryl + PEI + PEI (2 layers) | 6.09 ± 0.10 |

The other sample was used to immobilize $^{125}$I-BSA. Six PEI coated segments were cut (5×5 mm each) along with six untreated samples (5×5 mm) and reacted according to the following scheme:

| Group | Samples | Description |
| --- | --- | --- |
| 1 | V1–V3 | Untreated (control) |
| 2 | V4–V6 | Untreated (control) + sulfo-EGS |
| 3 | P1–P3 | Treated (control) |
| 4 | P4–P6 | Treated sample + sulfo-EGS |

The samples were placed in 0.2 ml of BSA solution (from 50 ml of 4 mg/ml BSA in PBS, pH 7.2, spiked with 100 μl of $^{125}$I-BSA, specific activity 156 cpm/μg) for 10 min., then 80 ml of sulfo-EGS solution (4.5 μg sulfo-EGS in 900 μl PBS, pH 7.2) were added to groups 2 and 4, and 80 μl of PBS were added to groups 1 and 3. The solutions were incubated for 30 min. at room temperature, the membranes were removed and individually washed twice in 0.5 ml PBS. The amount of protein attached to the membranes after rinsing was determined and is shown below:

| Group | Protein Attached (μg/cm$^2$) |
| --- | --- |
| 1 | 6.2 ± 1.4 |
| 2 | 8.5 ± 0.2 |
| 3 | 23.6 ± 1.4 |
| 4 | 21.9 ± 3.5 |

Example 27

This example describes a method for detecting amino groups by the presence of the nitrogen element after modifying a support to attach polylysine or polyethyleneimine layers to the support. Samples which do not contain nitrogen in the support (e.g. PLA and PGA) are analyzed by X-ray photoelectron spectroscopy to detect nitrogen in the first and/or second layers. It is expected that the analysis of surfaces containing polylysine or polyethyleneimine demonstrates the presence of nitrogen.

Example 28

This example describes a method for detecting hydroxyl groups by the presence of —OH (molecular weight: 17 g/mol) groups on the surface. Static Secondary Ion Mass Spectroscopy (static SIMS) is used to analyze the surface of modified samples. The presence of a peak at 17 atomic mass units (a.m.u.) is expected to indicate the presence of hydroxyl groups on a support which does not normally contain hydroxyl groups.

We claim:

1. A biodegradable material for immobilization of bioactive species thereon, the material comprising:
   a porous hydrophobic biodegradable support member;
   a first layer comprised of at least one species of a polymeric surfactant, wherein the polymeric surfactant is adsorbed to the support member, and wherein the surfactant is cross-linked to itself with a cross-linking agent that forms covalent bonds that are subject to enzymatic cleavage or non-enzymatic hydrolysis under in vivo conditions.

2. The biodegradable material of claim 1 further comprising at least one type of bioactive species attached to the first layer.

3. The biodegradable material of claim 2 wherein the bioactive species is recombinant human bone morphogenetic protein-2 (rhBMP-2).

4. The biodegradable material of claim 1 wherein the support member is selected from a member of the groups consisting of polyglycolide (PGA), copolymers of glycolide, glycolide/L-lactide copolymers (PGA/PLLA), lactide/trimethylene carbonate copolymers (PLA/TMC), glycolide/trimethylene carbonate copolymers (PGA/TMC), polylactides (PLA), stereo-copolymers of PLA, poly-L-lactide (PLLA), poly-DL-lactide (PDLLA), L-lactide/DL-lactide copolymers, copolymers of PLA, lactide/tetramethylglycolide copolymers, lactide/α-valerolactone copolymers, lactide/ε-caprolactone copolymers, PLA/polyethylene oxide copolymers, poly-βhydroxybutyrate (PHBA), PHBA/βhydroxyvalerate copolymers (PHBA/HVA), poly-p-dioxanone (PDS), poly-α-valerolactone, poly-ε-caprolactone, methylmethacrylate-N-vinyl-pyrrolidone copolymers, polyesters of oxalic acid, polyalkyl-2-cyanoacrylates, polyurethanes, and blends of the aforementioned polymers.

5. The biodegradable material of claim 1 wherein the support member is selected from a member of the groups consisting of polybutylene oxalate, polyethylene adipate, polyethylene carbonate, and polybutylene carbonate, and blends of the aforementioned polymers.

6. The biodegradable material of claim 1 wherein the support member is selected from a member of the groups consisting of polyesters containing silyl ethers and blends of the aforementioned polymers.

7. The biodegradable material of claim 1 wherein the polymeric surfactant is selected from the group consisting of polyvinyl alcohol, polyethylene glycol, polypropylene glycol, dextran, agarose, alginate, polyacrylamide, polyglycidol, polyvinyl alcohol-co-polyethylene, poly(vinyl acetate-co-vinyl alcohol), polyacrylic acid, polyamide, polypeptides, poly-lysine, polyethyleneimine, poly-β-malic acid, hyaluronic acid, derivatives of hyaluronic acid, and polyvinyl pyrrolidone, alone or in combination.

8. The biodegradable material of claim 1 wherein the polymeric surfactant comprises a polysaccharide.

9. The biodegradable material of claim 1 wherein the cross-linking agent comprises a compound having at least two chemically functional groups selected from the group consisting of aldehydes, epoxides, acyl halides, alkyl halides, isocyanates, amines, anhydrides, acids, alcohols, haloacetals, aryl carbonates, thiols, esters, imides, vinyls, azides, nitros, peroxides, sulfones, and maleimides.

10. The biodegradable material of claim 1 wherein the cross-linking agent is selected from the group consisting of poly(acrylic acid), vinyl sulfone, succinyl chloride, polyanhydrides, succinimidyl succinate-polyethylene glycol, and succinimidyl succinamide-polyethylene glycol.

11. The biodegradable material of claim 1 further comprising:
a second layer comprised of at least one species of a surfactant attached to the first layer.

12. The biodegradable material of claim 11 further comprising at least one type of bioactive species attached to the second layer.

13. The biodegradable material of claim 12 wherein the bioactive species is recombinant human bone morphogenetic protein-2 (rhBMP-2).

14. The biodegradable material of claim 1 wherein the surfactant of the second layer is selected from the group consisting of polyvinyl alcohol, polylysine, poly (acrylonitrile-co-acrylic acid-acrylamidine), polyacrylic acid, polyhydroxyethylmethacrylate, polyvinylpyrrolidone, polyethylene glycol, alginate, agarose, poly-β-malic acid, hyaluronic acid, derivatives of hyaluronic acid, polyacrolein, polyethyleneimine, polyallylamine, polyornithine, and their copolymers, either alone or in combination.

15. The biodegradable material of claim 2 wherein a spacer compound is interposed between the first layer and the bioactive species.

16. The biodegradable material of claim 15 wherein the spacer compound is selected from the group consisting of succinic acid, diaminohexane, glyoxylic acid, short chain polyethylene glycol, and glycine.

17. The biodegradable material of claim 15 wherein the spacer compound is cleavable.

18. The biodegradable material of claim 17 wherein the cleavable spacer compound is selected from the group consisting of polyhydroxyacids, polyanhydrides, polyamino acids, tartarates, and cysteine-linkers.

19. A biodegradable material having bioactive species immobilized thereon, the material comprising:
a porous hydrophobic biodegradable support member;
a first layer comprised of at least one species of a polymeric surfactant, wherein the polymeric surfactant is adsorbed to the support member, wherein the surfactant is cross-linked to itself through acid-base coacervation, carboxyic acid-ether complexation, ion complexation, ionic interactions, metal complexation, or alcoholic hydrogen bonding, and wherein the cross-linked surfactant is subject to degradation under in vivo conditions.

20. The biodegradable material of claim 19 further comprising at least one type of bioactive species attached to the first layer.

21. The biodegradable material of claim 20 wherein the bioactive species is recombinant human bone morphogenetic protein-2 (rhBMP-2).

22. The biodegradable material of claim 19 wherein the support member is selected from a member of the groups consisting of polyglycolide (PGA), copolymers of glycolide, glycolide/L-lactide copolymers (PGA/PLLA), lactide/ trimethylene carbonate copolymers (PLA/TMC), glycolide/ trimethylene carbonate copolymers (PGA/TMC), polylactides (PLA), stereo-copolymers of PLA, poly-L-lactide (PLLA), poly-DL-lactide (PDLLA), L-lactide/DL-lactide copolymers, copolymers of PLA, lactide/ tetramethylglycolide copolymers, lactide/(α-valerolactone copolymers, lactide/ε-caprolactone copolymers, PLA/ polyethylene oxide copolymers, poly-βhydroxybutyrate (PHBA), PHBA/βhydroxyvalerate copolymers (PHBA/ HVA), poly-p-dioxanone (PDS), poly-α-valerolactone, poly-ε-caprolactone, methylmethacrylate-N-vinyl-pyrrolidone copolymers, polyesters of oxalic acid, polyalkyl-2-cyanoacrylates, polyurethanes, and blends of the aforementioned polymers.

23. The biodegradable material of claim 19 wherein the support member is selected from a member of the groups consisting of polybutylene oxalate, polyethylene adipate, polyethylene carbonate, and polybutylene carbonate, and blends of the aforementioned polymers.

24. The biodegradable material of claim 19 wherein the support member is selected from a member of the groups consisting of polyesters containing silyl ethers and blends of the aforementioned polymers.

25. The biodegradable material of claim 19 wherein the polymeric surfactant is selected from the group consisting of polyvinyl alcohol, polyethylene glycol, polypropylene glycol, dextran, agarose, alginate, polyacrylamide, polyglycidol, polyvinyl alcohol-co-polyethylene, poly (ethyleneglycol-co-propyleneglycol), poly(vinyl acetate-co-vinyl alcohol), polyacrylic acid, polypeptides, poly-lysine, polyethyleneimine, poly-β-malic acid, hyaluronic acid, derivatives of hyaluronic acid, and polyvinyl pyrrolidone, alone or in combination.

26. The biodegradable material of claim 19 wherein the polymeric surfactant comprises a polysaccharide.

27. The biodegradable material of claim 19 further comprising:
a second layer comprised of at least one species of a surfactant attached to the first layer.

28. The biodegradable material of claim 27 further comprising at least one type of bioactive species attached to the second layer.

29. The biodegradable material of claim 28 wherein the bioactive species is recombinant human bone morphogenetic protein-2 (rhBMP-2).

30. The biodegradable material of claim 27 wherein the surfactant of the second layer is selected from the group consisting of polyvinyl alcohol, polylysine, polyacrylic acid, polyvinylpyrrolidone, polyethylene glycol, alginate, agarose, poly-β-malic acid, hyaluronic acid, derivatives of hyaluronic acid, polyethyleneimine, polyallylamine, polyornithine, and their copolymers, either alone or in combination.

31. The biodegradable material of claim 28 wherein a spacer compound is interposed between the first layer and the bioactive species.

32. The biodegradable material of claim 31 wherein the spacer compound is selected from the group consisting of succinic acid, diaminohexane, glyoxylic acid, short chain polyethylene glycol, and glycine.

33. The biodegradable material of claim 31 wherein the spacer compound is cleavable.

34. The biodegradable material of claim 33 wherein the cleavable spacer compound is selected from the group consisting of polyhydroxyacids, polyanhydrides, polyamino acids, tartarates, and cysteine-linkers.

35. A method of making a material for the immobilization of bioactive species thereon, the method comprising:
providing a porous hydrophobic biodegradable support member;
adsorbing a first layer comprised of at least one type of polymeric surfactant to the support member; and
cross-linking the polymeric surfactant to itself with chemical bonds that are subject to degradation in a recipient.

36. The method of claim 35 further comprising attaching at least one type of bioactive species to the first layer.

37. The biodegradable material of claim 36 wherein the bioactive species is recombinant human bone morphogenetic protein-2 (rhBMP-2).

38. The method of claim 35 wherein the polymeric surfactant is cross-linked with a cross-linking agent.

39. The method of claim 35 wherein the polymeric surfactant is cross-linked with non-covalent bonds.

40. The method of claim 39 wherein the polymeric surfactant is cross-linked via cyano polar interactions.

41. The method of claim 39 wherein the polymeric surfactant is cross-linked by acid-base coacervation.

42. The method of claim 39 wherein the polymeric surfactant is cross-linked by carboxylic acid-ether complexation.

43. The method of claim 39 wherein the polymeric surfactant is cross-linked by ion complexation.

44. The method of claim 39 wherein the polymeric surfactant is cross-linked by metal complexation.

45. The method of claim 39 wherein the polymeric surfactant is cross-linked by alcoholic hydrogen bonding.

46. The method of claim 35 further comprising:
attaching a second layer comprised of at least one type of surfactant to the first layer.

47. The method of claim 46 further comprising attaching at least one type of bioactive species to the first layer.

48. The biodegradable material of claim 47 wherein the bioactive species is recombinant human bone morphogenetic protein-2 (rhBMP-2).

49. The method of claim 35 wherein the polymeric surfactants are selected from a member of the group consisting of polyvinyl alcohol, polyethylene glycol, polypropylene glycol, dextran, agarose, alginate, polyacrylamide, polyglycidol, polyvinyl alcohol-co-polyethylene, poly(ethyleneglycol-co-propyleneglycol), poly(vinyl acetate-co-vinyl alcohol), poly(tetrafluoroethylene-co-vinyl alcohol), poly(acrylonitrile-co-acrylamide), poly(acrylonitrile-co-acrylic acid-acrylamidine), polyacrylic acid, poly-lysine, polyethyleneimine, polyvinyl pyrrolidone, poly-b-malic acid, hyaluronic acid, derivatives of hyaluronic acid, polyhydroxyethylmethacrylate, and polysaccharides, and their copolymers, either alone or in combination.

50. The method of claim 46 wherein the surfactant of the second layer is selected from the group consisting of polyvinyl alcohol, polylysine, poly(acrylonitrile-co-acrylic acid-acrylamidine), polyacrylic acid, polyhydroxyethylmethacrylate polyvinylpyrrolidone, polyethylene glycol, alginate, agarose, poly-β-malic acid, hyaluronic acid, derivatives of hyaluronic acid, polyacrolein, polyethyleneimine, polyallylamine, polyornithine, and their copolymers, either alone or in combination.

51. The method of claim 38 wherein the cross-linking agent is selected from a member of the group consisting of vinyls, imidazoles, carbamates, aldehydes, epoxides, acyl halides, akyl halides, isocyanates, amines, anhydrides, acids, alcohols, thiols, esters, imides, and maleimides.

52. The method of claim 38 further comprising:
using a sufficient amount of cross-linking agent when cross-linking the polymeric surfactants so that unreacted chemically reactive groups of the cross-linking agent are present.

53. The method of claim 38 further comprising:
cross-linking the polymeric surfactants with a cross-linking agent under conditions that do not produce polymerization of the cross-linking agent.

54. The method of claim 38 further comprising:
using a catalyst with the cross-linking agent that evolves as a gas following the cross-linking step.

55. The biodegradable material of claim 1 wherein the material is produced through the following process:
providing a porous hydrophobic biodegradable support member;
adsorbing a first layer comprised of at least one species of a polymeric surfactant to the support member; and
cross-linking the polymeric surfactant to itself with chemical bonds that are subject to degradation in a recipient.

56. The method of claim 55 further comprising attaching at least one type of bioactive species to the first layer.

57. The biodegradable material of claim 56 wherein the bioactive species is recombinant human bone morphogenetic protein-2 (rhBMP-2).

58. The biodegradable material of claim 55 further comprising:
attaching a second layer comprised of at least one type of surfactant to the first layer.

59. The method of claim 55 further comprising attaching at least one type of bioactive species to the first layer.

60. The biodegradable material of claim 59 wherein the bioactive species is recombinant human bone morphogenetic protein-2 (rhBMP-2).

61. The material of claim 55 wherein the porous support member is selected from a member of the group consisting of porous polyglycolide (PGA), porous copolymers of glycolide, porous glycolide/L-lactide copolymers (PGA/PLLA), porous lactide/trimethylene carbonate copolymers (PLA/TMC), porous glycolide/trimethylene carbonate copolymers (PGA/TMC), porous polylactides (PLA), porous stereo-copolymers of PLA, porous poly-L-lactide (PLLA), porous poly-DL-lactide (PDLLA), porous L-lactide/DL-lactide copolymers, porous copolymers of PLA, porous lactide/tetramethylglycolide copolymers, porous lactide/α-valerolactone copolymers, porous lactide/ε-caprolactone copolymers, porous PLA/polyethylene oxide copolymers, porous poly-βhydroxybutyrate (PHBA), porous PHBA/βhydroxyvalerate copolymers (PHBA/HVA), porous poly-p-dioxanone (PDS), porous poly-α-valerolactone, porous poly-ε-caprolactone, porous methylmethacrylate-N-vinyl-pyrrolidone copolymers, porous polyesters of oxalic acid, porous polyalkyl-2-cyanoacrylates, and blends of the aforementioned polymers.

62. The material of claim 55 wherein the polymeric surfactant comprises a multifunctional copolymer comprised of at least one domain having a physicochemical affinity for the support member and at least one domain that is chemically reactive with a cross-linking agent.

63. The method of claim 58 wherein the surfactant of the second layer is selected from the group consisting of polyvinyl alcohol, polylysine, poly(acrylonitrile-co-acrylic acid-acrylamidine), polyacrylic acid, polyhydroxymethylmethacrylate polyvinylpyrrolidone, polyethylene glycol, alginate, agarose, poly-β-malic acid, hyaluronic acid, derivatives of hyaluronic acid, polyacrolein, polyethyleneimine, polyallylamine, polyornithine, and their copolymers, either alone or in combination.

64. The material of claim 55 wherein a spacer compound is interposed between the first layer and the bioactive species.

65. The material of claim 64 wherein the spacer compound is selected from a member of a group consisting of succinic acid, diaminohexane, glyoxylic acid, short chain polyethylene glycol, and glycine.

66. The material of claim 64 wherein the spacer compound is cleavable.

67. The material of claim 66 wherein the cleavable spacer compound is selected from the group consisting of polyhydroxyacids, polyanhydrides, polyamino acids, tartarates, and cysteine-linkers.

68. A biodegradable material for immobilization of bioactive species thereon, the material comprising:

a support member comprising poly(glycolic acid); and a first layer comprising poly(ethyleneimine) adsorbed to the support member, wherein the poly(ethyleneimine) is cross-linked to itself with a cross-linking agent that forms covalent bonds that are subject to enzymatic cleavage or non-enzymatic hydrolysis.

69. The biodegradable material of claim 68 further comprising a second layer comprising poly(ethyleneimine) attached to the first layer.

70. The biodegradable material of claim 68 further comprising a bioactive species attached to the first layer, the bioactive species comprising a polypeptide having an amino acid sequence comprising arginine, glycine, and aspartic acid.

71. The biodegradable material of claim 69 further comprising a bioactive species attached to the second layer, the bioactive species comprising a polypeptide having an amino acid sequence comprising arginine, glycine, and aspartic acid.

72. A biodegradable material for immobilization of bioactive species thereon, the material comprising:

a support member comprising a copolymer of glycolide and trimethylene carbonate; and a first layer comprising poly(ethyleneimine) adsorbed to the support member, wherein the poly(ethyleneimine) is cross-linked to itself with a cross-linking agent that forms covalent bonds that are subject to enzymatic cleavage or non-enzymatic hydrolysis.

73. The biodegradable material of claim 72 further comprising a second layer comprising poly(ethyleneimine) attached to the first layer.

74. The biodegradable material of claim 72 further comprising a bioactive species attached to the first layer, the bioactive species comprising a polypeptide having an amino acid sequence comprising arginine, glycine, and aspartic acid.

75. The biodegradable material of claim 73 further comprising a bioactive species attached to the second layer, the bioactive species comprising a polypeptide having an amino acid sequence comprising arginine, glycine, and aspartic acid.

* * * * *